US010722480B2

(12) United States Patent
Terashima et al.

(10) Patent No.: US 10,722,480 B2
(45) Date of Patent: Jul. 28, 2020

(54) AGENT FOR CONTROLLING CELLS CONSTITUTING CANCER MICROENVIRONMENT OR INFLAMMATORY MICROENVIRONMENT

(71) Applicant: The University of Tokyo, Tokyo (JP)

(72) Inventors: Yuya Terashima, Tokyo (JP); Kouji Matsushima, Tokyo (JP); Etsuko Toda, Tokyo (JP); Hiroaki Terasawa, Kumamoto (JP); Sosuke Yoshinaga, Kumamoto (JP)

(73) Assignee: TOKYO UNIVERSITY OF SCIENCE FOUNDATION, Tokyo (JP)

( * ) Notice: Subject to any disclaimer, the term of this patent is extended or adjusted under 35 U.S.C. 154(b) by 0 days.

(21) Appl. No.: 15/542,028

(22) PCT Filed: Jan. 6, 2016

(86) PCT No.: PCT/JP2016/050214
§ 371 (c)(1),
(2) Date: Aug. 8, 2017

(87) PCT Pub. No.: WO2016/111307
PCT Pub. Date: Jul. 14, 2016

(65) Prior Publication Data
US 2018/0000755 A1    Jan. 4, 2018

(30) Foreign Application Priority Data
Jan. 6, 2015  (JP) ................. 2015-000978

(51) Int. Cl.
| *A61K 31/145* | (2006.01) |
| *G16B 15/00* | (2019.01) |
| *A61K 45/06* | (2006.01) |
| *C12Q 1/32* | (2006.01) |
| *G01N 33/68* | (2006.01) |

(52) U.S. Cl.
CPC ............ *A61K 31/145* (2013.01); *A61K 45/06* (2013.01); *C12Q 1/32* (2013.01); *C12Y 102/01003* (2013.01); *G01N 33/6863* (2013.01); *G16B 15/00* (2019.02); *G01N 2333/521* (2013.01); *G01N 2333/7158* (2013.01); *G01N 2500/02* (2013.01); *G01N 2500/20* (2013.01)

(58) Field of Classification Search
None
See application file for complete search history.

(56) References Cited

U.S. PATENT DOCUMENTS

2001/0016600 A1    8/2001  Kennedy

FOREIGN PATENT DOCUMENTS

| JP | 2004-525079 A | 8/2004 |
| JP | 2013-100268 A | 5/2013 |
| JP | 5424960 B2 | 2/2014 |

OTHER PUBLICATIONS

Cen et al (J Med Chem 47:6914-6920, 2004) (Year: 2004).*
Simeone et al (J Immunotoxicology 9:241-247, 2012) (Year: 2012).*
Cen et al., "Disulfiram Induces Apoptosis in Human Melanoma Cells: A Redox-related Process," Molecular Cancer Therapeutics, vol. 1, Jan. 2002, pp. 197-204 (9 pages total).
Chen et al. "Disulfiram, a Clinically Used Anti-Alcoholism Drug and Copper-Binding Agent, Induces Apoptotic Cell Death in Breast Cancer Cultures and Xenografts via Inhibition of the Proteasome Activity," Cancer Res, vol. 66, No. 21, Nov. 1, 2006, pp. 10425-10433 (10 pages total).
Duan et al., "Multi-targeted Inhibition of Tumor Growth and Lung Metastasis by Redox-sensitive Shell Crosslinked Micelles Loading Disulfiram," Nanotechnology, vol. 25, No. 12, Mar. 2014 (Published Feb. 27, 2014), 15 pages.
Esaki et al., "Structural Analyses of the Interaction of Chemokine Receptor CCR2/CCR5 and FROUNT: Novel Therapeutic Target Molecules in Chronic Inflammation," Endocrinology, Diabetology & Metabolism, vol. 35, No. 6, Dec. 2012, pp. 500-507 (17 pages total), with an English translation.
Iljin et al., "High-Throughput Cell-Based Screening of 4910 Known Drugs and Drug-like Small Molecules Identifies Disulfiram as an Inhibitor of Prostate Cancer Cell Growth," Clin Cancer Res, vol. 15, No. 19, Oct. 1, 2009 (Published Online First Sep. 29, 2009), pp. 6070-6078 (10 pages).
Kiyogi et al., "Paradigm Shift from Chemokines to Frount, a Receptor Signal Regulatory Molecule," Gan Kiban Seibutsugaku— Kakushinteki Seeds Ikusei Ni Mukete (Cancer Basic Biology— Towards Cultivation Innovative Seeds), 2013, pp. 130-136 (15 pages total), with English translation.
Nechushtan et al., "A Phase IIb Trial Assessing the Addition of Disulfirarn to Chemotherapy for the Treatment of Metastatic Non-Small Cell Lung Cancer," The Oncologist, vol. 20, 2015, pp. 366 367.
Terashima et al., "Development of Anti-inflammatory Drug Targeting Chemokine Receptor and Frount Interaction which Regulates Chemotaxis Signaling," Inflammation Research, vol. 60, No. 6, Suppl. 1, P-068, Jun. 2011, pp. 5104 (4 pages total).

(Continued)

*Primary Examiner* — Craig D Ricci
(74) *Attorney, Agent, or Firm* — Birch, Stewart, Kolasch & Birch, LLP

(57) ABSTRACT

An agent according to the present invention comprises as an effective component any of (1) disulfiram, diethyldithiocarbamate, or a metal complex of diethyldithiocarbamate; (2) a pharmaceutically acceptable salt of (1); or (3) a solvate of (1) or (2), and is used for inhibition of interaction between CR2B or CCR5 and FROUNT protein, inhibition of macrophages, control of cells constituting a cancer microenvironment or inflammatory microenvironment, or enhancement of anticancer activity of an anticancer drug. It is also possible to provide a compound with a reduced side effect and an increased pharmacological effect by identifying a disulfiram derivative having a lower aldehyde dehydrogenase-inhibiting activity and a higher FROUNT-inhibiting activity among derivatives prepared by structural modification of disulfiram.

1 Claim, 7 Drawing Sheets

Specification includes a Sequence Listing.

(56) References Cited

OTHER PUBLICATIONS

Terashima et al., "Pivotal Function for Cytoplasmic Protein FROUNT in CCR2-mediated Monocyte Chemotaxis," Nature Immunology, vol. 6, No. 8, Aug. 2005 (Published online Jul. 3, 2005), pp. 827-835.

Toda et al., "FROUNT Is a Common Regulator of CCR2 and CCR5 Signaling to Control Directional Migration," The Journal of Immunology, vol. 183, 2009 (Prepublished online Oct. 19, 2009), pp. 6387-6394 (9 pages total).

Written Opinion of the International Searching Authority and International Search Report (forms PCT/ISA/237 and PCT/ISA/210), dated Mar. 15, 2016, for International Application No. PCT/JP2016/050214, along with an English translation of the Written Opinion.

\* cited by examiner

Lewis lung carcinoma

SEQUENCE LISTING

```
<160> NUMBER OF SEQ ID NOS: 8

<210> SEQ ID NO 1
<211> LENGTH: 1971
<212> TYPE: DNA
<213> ORGANISM: Homo sapiens
<220> FEATURE:
<221> NAME/KEY: CDS
<222> LOCATION: (1)..(1971)

<400> SEQUENCE: 1 atg gag gag ctc gat ggc gag cca aca gtc act ttg att cca ggc gtg      48
```

```
                Met Glu Glu Leu Asp Gly Glu Pro Thr Val Thr Leu Ile Pro Gly Val
                1               5                   10                  15 aat tcc aag aag aac caa atg tat ttt gac tgg ggt cca ggg gag atg              96
Asn Ser Lys Lys Asn Gln Met Tyr Phe Asp Trp Gly Pro Gly Glu Met
                20                  25                  30 ctg gta tgt gaa acc tcc ttc aac aaa aaa gaa aaa tca gag atg gtg             144
Leu Val Cys Glu Thr Ser Phe Asn Lys Lys Glu Lys Ser Glu Met Val
            35                  40                  45 cca agt tgc ccc ttt atc tat atc atc cgt aag gat gta gat gtt tac             192
Pro Ser Cys Pro Phe Ile Tyr Ile Ile Arg Lys Asp Val Asp Val Tyr
        50                  55                  60 tct caa atc ttg aga aaa ctc ttc aat gaa tcc cat gga atc ttt ctg             240
Ser Gln Ile Leu Arg Lys Leu Phe Asn Glu Ser His Gly Ile Phe Leu
65                  70                  75                  80 ggc ctc cag aga att gac gaa gag ttg act gga aaa tcc aga aaa tct             288
Gly Leu Gln Arg Ile Asp Glu Glu Leu Thr Gly Lys Ser Arg Lys Ser
                85                  90                  95 caa ttg gtt cga gtg agt aaa aac tac cga tca gtc atc aga gca tgt             336
Gln Leu Val Arg Val Ser Lys Asn Tyr Arg Ser Val Ile Arg Ala Cys
            100                 105                 110 atg gag gaa atg cac cag gtt gca att gct gct aaa gat cca gcc aat             384
Met Glu Glu Met His Gln Val Ala Ile Ala Ala Lys Asp Pro Ala Asn
        115                 120                 125 ggc cgc cag ttc agc agc cag gtc tcc att ttg tca gca atg gag ctc             432
Gly Arg Gln Phe Ser Ser Gln Val Ser Ile Leu Ser Ala Met Glu Leu
    130                 135                 140 atc tgg aac ctg tgt gag att ctt ttt att gaa gtg gcc cca gct ggc             480
Ile Trp Asn Leu Cys Glu Ile Leu Phe Ile Glu Val Ala Pro Ala Gly
145                 150                 155                 160 cct ctc ctc ctc cat ctc ctt gac tgg gtc cgg ctc cat gtg tgc gag             528
Pro Leu Leu Leu His Leu Leu Asp Trp Val Arg Leu His Val Cys Glu
                165                 170                 175 gtg gac agt ttg tcg gca gat gtt ctg ggc agt gag aat cca agc aaa             576
Val Asp Ser Leu Ser Ala Asp Val Leu Gly Ser Glu Asn Pro Ser Lys
            180                 185                 190 cat gac agc ttc tgg aac ttg gtg acc atc ttg gtg ctg cag ggc cgg             624
His Asp Ser Phe Trp Asn Leu Val Thr Ile Leu Val Leu Gln Gly Arg
        195                 200                 205 ctg gat gag gcc cga cag atg ctc tcc aag gaa gcc gat gcc agc ccc             672
Leu Asp Glu Ala Arg Gln Met Leu Ser Lys Glu Ala Asp Ala Ser Pro
    210                 215                 220 gcc tct gca ggc ata tgc cga atc atg ggg gac ctg atg agg aca atg             720
Ala Ser Ala Gly Ile Cys Arg Ile Met Gly Asp Leu Met Arg Thr Met
225                 230                 235                 240 ccc att ctt agt cct ggg aac acc cag aca ctg aca gag ctg gag ctg             768
Pro Ile Leu Ser Pro Gly Asn Thr Gln Thr Leu Thr Glu Leu Glu Leu
                245                 250                 255 aag tgg cag cac tgg cac gag gaa tgt gag cgg tac ctc cag gac agc             816
Lys Trp Gln His Trp His Glu Glu Cys Glu Arg Tyr Leu Gln Asp Ser
            260                 265                 270 aca ttc gcc acc agc cct cac ctg gag tct ctc ttg aag att atg ctg             864
Thr Phe Ala Thr Ser Pro His Leu Glu Ser Leu Leu Lys Ile Met Leu
        275                 280                 285 gga gac gaa gct gcc ttg tta gag cag aag gaa ctt ctg agt aat tgg             912
Gly Asp Glu Ala Ala Leu Leu Glu Gln Lys Glu Leu Leu Ser Asn Trp
    290                 295                 300 tat cat ttc cta gtg act cgg ctc ttg tac tcc aat ccc aca gta aaa             960
Tyr His Phe Leu Val Thr Arg Leu Leu Tyr Ser Asn Pro Thr Val Lys
305                 310                 315                 320
```

-continued

| | | |
|---|---|---|
| ccc att gat ctg cac tac tat gcc cag tcc agc ctg gac ctg ttt ctg<br>Pro Ile Asp Leu His Tyr Tyr Ala Gln Ser Ser Leu Asp Leu Phe Leu<br>325 330 335 | | 1008 |
| gga ggt gag agc agc cca gaa ccc ctg gac aac atc ttg ttg gca gcc<br>Gly Gly Glu Ser Ser Pro Glu Pro Leu Asp Asn Ile Leu Leu Ala Ala<br>340 345 350 | | 1056 |
| ttt gag ttt gac atc cat caa gta atc aaa gag tgc agc atc gcc ctg<br>Phe Glu Phe Asp Ile His Gln Val Ile Lys Glu Cys Ser Ile Ala Leu<br>355 360 365 | | 1104 |
| agc aac tgg tgg ttt gtg gcc cac ctg aca gac ctg ctg gac cac tgc<br>Ser Asn Trp Trp Phe Val Ala His Leu Thr Asp Leu Leu Asp His Cys<br>370 375 380 | | 1152 |
| aag ctc ctc cag tca cac aac ctc tat ttc ggt tcc aac atg aga gag<br>Lys Leu Leu Gln Ser His Asn Leu Tyr Phe Gly Ser Asn Met Arg Glu<br>385 390 395 400 | | 1200 |
| ttc ctc ctg ctg gag tac gcc tcg gga ctg ttt gct cat ccc agc ctg<br>Phe Leu Leu Leu Glu Tyr Ala Ser Gly Leu Phe Ala His Pro Ser Leu<br>405 410 415 | | 1248 |
| tgg cag ctg ggg gtc gat tac ttt gat tac tgc ccc gag ctg ggc cga<br>Trp Gln Leu Gly Val Asp Tyr Phe Asp Tyr Cys Pro Glu Leu Gly Arg<br>420 425 430 | | 1296 |
| gtc tcc ctg gag ctg cac att gag cgg ata cct ctg aac acc gag cag<br>Val Ser Leu Glu Leu His Ile Glu Arg Ile Pro Leu Asn Thr Glu Gln<br>435 440 445 | | 1344 |
| aaa gcc ctg aag gtg ctg cgg atc tgt gag cag cgg cag atg act gaa<br>Lys Ala Leu Lys Val Leu Arg Ile Cys Glu Gln Arg Gln Met Thr Glu<br>450 455 460 | | 1392 |
| caa gtt cgc agc att tgt aag atc tta gcc atg aaa gcc gtc cgc aac<br>Gln Val Arg Ser Ile Cys Lys Ile Leu Ala Met Lys Ala Val Arg Asn<br>465 470 475 480 | | 1440 |
| aat cgc ctg ggt tct gcc ctc tct tgg agc atc cgt gct aag gat gcc<br>Asn Arg Leu Gly Ser Ala Leu Ser Trp Ser Ile Arg Ala Lys Asp Ala<br>485 490 495 | | 1488 |
| gcc ttt gcc acg ctc gtg tca gac agg ttc ctc agg gat tac tgt gag<br>Ala Phe Ala Thr Leu Val Ser Asp Arg Phe Leu Arg Asp Tyr Cys Glu<br>500 505 510 | | 1536 |
| cga ggc tgc ttt tct gat ttg gat ctc att gac aac ctg ggg cca gcc<br>Arg Gly Cys Phe Ser Asp Leu Asp Leu Ile Asp Asn Leu Gly Pro Ala<br>515 520 525 | | 1584 |
| atg atg ctc agt gac cga ctg aca ttc ctg gga aag tat cgc gag ttc<br>Met Met Leu Ser Asp Arg Leu Thr Phe Leu Gly Lys Tyr Arg Glu Phe<br>530 535 540 | | 1632 |
| cac cgt atg tac ggg gag aag cgt ttt gcc gac gca gct tct ctc ctt<br>His Arg Met Tyr Gly Glu Lys Arg Phe Ala Asp Ala Ala Ser Leu Leu<br>545 550 555 560 | | 1680 |
| ctg tcc ttg atg acg tct cgg att gcc cct cgg tct ttc tgg atg act<br>Leu Ser Leu Met Thr Ser Arg Ile Ala Pro Arg Ser Phe Trp Met Thr<br>565 570 575 | | 1728 |
| ctg ctg aca gat gcc ttg ccc ctt ttg gaa cag aaa cag gtg att ttc<br>Leu Leu Thr Asp Ala Leu Pro Leu Leu Glu Gln Lys Gln Val Ile Phe<br>580 585 590 | | 1776 |
| tca gca gaa cag act tat gag ttg atg cgg tgt ctg gag gac ttg acg<br>Ser Ala Glu Gln Thr Tyr Glu Leu Met Arg Cys Leu Glu Asp Leu Thr<br>595 600 605 | | 1824 |
| tca aga aga cct gtg cat gga gaa tct gat acc gag cag ctc cag gat<br>Ser Arg Arg Pro Val His Gly Glu Ser Asp Thr Glu Gln Leu Gln Asp<br>610 615 620 | | 1872 |
| gat gac ata gag acc acc aag gtg gaa atg ctg aga ctt tct ctg gca<br>Asp Asp Ile Glu Thr Thr Lys Val Glu Met Leu Arg Leu Ser Leu Ala<br>625 630 635 640 | | 1920 |

```
cga aat ctt gct cgg gca att ata aga gaa ggc tca ctg gaa ggt tcc    1968
Arg Asn Leu Ala Arg Ala Ile Ile Arg Glu Gly Ser Leu Glu Gly Ser
            645                 650                 655 tga                                                                 1971
```

<210> SEQ ID NO 2
<211> LENGTH: 656
<212> TYPE: PRT
<213> ORGANISM: Homo sapiens

<400> SEQUENCE: 2

```
Met Glu Glu Leu Asp Gly Glu Pro Thr Val Thr Leu Ile Pro Gly Val
1               5                   10                  15

Asn Ser Lys Lys Asn Gln Met Tyr Phe Asp Trp Gly Pro Gly Glu Met
            20                  25                  30

Leu Val Cys Glu Thr Ser Phe Asn Lys Lys Glu Lys Ser Glu Met Val
        35                  40                  45

Pro Ser Cys Pro Phe Ile Tyr Ile Ile Arg Lys Asp Val Asp Val Tyr
    50                  55                  60

Ser Gln Ile Leu Arg Lys Leu Phe Asn Glu Ser His Gly Ile Phe Leu
65                  70                  75                  80

Gly Leu Gln Arg Ile Asp Glu Glu Leu Thr Gly Lys Ser Arg Lys Ser
                85                  90                  95

Gln Leu Val Arg Val Ser Lys Asn Tyr Arg Ser Val Ile Arg Ala Cys
            100                 105                 110

Met Glu Glu Met His Gln Val Ala Ile Ala Ala Lys Asp Pro Ala Asn
        115                 120                 125

Gly Arg Gln Phe Ser Ser Gln Val Ser Ile Leu Ser Ala Met Glu Leu
    130                 135                 140

Ile Trp Asn Leu Cys Glu Ile Leu Phe Ile Glu Val Ala Pro Ala Gly
145                 150                 155                 160

Pro Leu Leu Leu His Leu Leu Asp Trp Val Arg Leu His Val Cys Glu
                165                 170                 175

Val Asp Ser Leu Ser Ala Asp Val Leu Gly Ser Glu Asn Pro Ser Lys
            180                 185                 190

His Asp Ser Phe Trp Asn Leu Val Thr Ile Leu Val Leu Gln Gly Arg
        195                 200                 205

Leu Asp Glu Ala Arg Gln Met Leu Ser Lys Glu Ala Asp Ala Ser Pro
    210                 215                 220

Ala Ser Ala Gly Ile Cys Arg Ile Met Gly Asp Leu Met Arg Thr Met
225                 230                 235                 240

Pro Ile Leu Ser Pro Gly Asn Thr Gln Thr Leu Thr Glu Leu Glu Leu
                245                 250                 255

Lys Trp Gln His Trp His Glu Glu Cys Glu Arg Tyr Leu Gln Asp Ser
            260                 265                 270

Thr Phe Ala Thr Ser Pro His Leu Glu Ser Leu Leu Lys Ile Met Leu
        275                 280                 285

Gly Asp Glu Ala Ala Leu Leu Glu Gln Lys Glu Leu Leu Ser Asn Trp
    290                 295                 300

Tyr His Phe Leu Val Thr Arg Leu Leu Tyr Ser Asn Pro Thr Val Lys
305                 310                 315                 320

Pro Ile Asp Leu His Tyr Tyr Ala Gln Ser Ser Leu Asp Leu Phe Leu
                325                 330                 335

Gly Gly Glu Ser Ser Pro Glu Pro Leu Asp Asn Ile Leu Leu Ala Ala
```

```
                340                 345                 350
Phe Glu Phe Asp Ile His Gln Val Ile Lys Glu Cys Ser Ile Ala Leu
            355                 360                 365

Ser Asn Trp Trp Phe Val Ala His Leu Thr Asp Leu Leu Asp His Cys
370                 375                 380

Lys Leu Leu Gln Ser His Asn Leu Tyr Phe Gly Ser Asn Met Arg Glu
385                 390                 395                 400

Phe Leu Leu Leu Glu Tyr Ala Ser Gly Leu Phe Ala His Pro Ser Leu
                405                 410                 415

Trp Gln Leu Gly Val Asp Tyr Phe Asp Tyr Cys Pro Glu Leu Gly Arg
            420                 425                 430

Val Ser Leu Glu Leu His Ile Glu Arg Ile Pro Leu Asn Thr Glu Gln
            435                 440                 445

Lys Ala Leu Lys Val Leu Arg Ile Cys Glu Gln Arg Gln Met Thr Glu
        450                 455                 460

Gln Val Arg Ser Ile Cys Lys Ile Leu Ala Met Lys Ala Val Arg Asn
465                 470                 475                 480

Asn Arg Leu Gly Ser Ala Leu Ser Trp Ser Ile Arg Ala Lys Asp Ala
                485                 490                 495

Ala Phe Ala Thr Leu Val Ser Asp Arg Phe Leu Arg Asp Tyr Cys Glu
            500                 505                 510

Arg Gly Cys Phe Ser Asp Leu Asp Leu Ile Asp Asn Leu Gly Pro Ala
            515                 520                 525

Met Met Leu Ser Asp Arg Leu Thr Phe Leu Gly Lys Tyr Arg Glu Phe
        530                 535                 540

His Arg Met Tyr Gly Glu Lys Arg Phe Ala Asp Ala Ala Ser Leu Leu
545                 550                 555                 560

Leu Ser Leu Met Thr Ser Arg Ile Ala Pro Arg Ser Phe Trp Met Thr
                565                 570                 575

Leu Leu Thr Asp Ala Leu Pro Leu Leu Glu Gln Lys Gln Val Ile Phe
            580                 585                 590

Ser Ala Glu Gln Thr Tyr Glu Leu Met Arg Cys Leu Glu Asp Leu Thr
            595                 600                 605

Ser Arg Arg Pro Val His Gly Glu Ser Asp Thr Glu Gln Leu Gln Asp
        610                 615                 620

Asp Asp Ile Glu Thr Thr Lys Val Glu Met Leu Arg Leu Ser Leu Ala
625                 630                 635                 640

Arg Asn Leu Ala Arg Ala Ile Ile Arg Glu Gly Ser Leu Glu Gly Ser
                645                 650                 655

<210> SEQ ID NO 3
<211> LENGTH: 16
<212> TYPE: PRT
<213> ORGANISM: Artificial Sequence
<220> FEATURE:
<223> OTHER INFORMATION: CCR2 pro-C peptide

<400> SEQUENCE: 3

Glu Lys Phe Arg Arg Tyr Leu Ser Val Phe Phe Arg Lys His Ile Thr
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: CCR5 pro-C peptide
```

<400> SEQUENCE: 4

Glu Lys Phe Arg Asn Tyr Leu Leu Val Phe Phe Gln Lys His Ile Ala
1               5                   10                  15

<210> SEQ ID NO 5
<211> LENGTH: 2335
<212> TYPE: DNA
<213> ORGANISM: Homo sapiens
<220> FEATURE:
<221> NAME/KEY: CDS
<222> LOCATION: (486)..(1568)

<400> SEQUENCE: 5

```
tttattctct ggaacatgaa acattctgtt gtgctcatat catgcaaatt atcactagta      60
ggagagcaga gagtggaaat gttccaggta taaagaccca caagataaag aagctcagag     120
tcgttagaaa caggagcaga tgtacagggt ttgcctgact cacactcaag gttgcataag     180
caagatttca aaattaatcc tattctggag acctcaaccc aatgtacaat gttcctgact     240
ggaaaagaag aactatattt ttctgatttt ttttttcaaa tctttaccat tagttgccct     300
gtatctccgc cttcactttc tgcaggaaac tttatttcct acttctgcat gccaagtttc     360
tacctctaga tctgtttggt tcagttgctg agaagcctga cataccagga ctgcctgaga     420
caagccacaa gctgaacaga gaaagtggat tgaacaagga cgcatttccc cagtacatcc     480
``` acaac atg ctg tcc aca tct cgt tct cgg ttt atc aga aat acc aac gag     530
      Met Leu Ser Thr Ser Arg Ser Arg Phe Ile Arg Asn Thr Asn Glu
      1               5                   10                  15 agc ggt gaa gaa gtc acc acc ttt ttt gat tat gat tac ggt gct ccc     578
Ser Gly Glu Glu Val Thr Thr Phe Phe Asp Tyr Asp Tyr Gly Ala Pro
                20                  25                  30 tgt cat aaa ttt gac gtg aag caa att ggg gcc caa ctc ctg cct ccg     626
Cys His Lys Phe Asp Val Lys Gln Ile Gly Ala Gln Leu Leu Pro Pro
        35                  40                  45 ctc tac tcg ctg gtg ttc atc ttt ggt ttt gtg ggc aac atg ctg gtc     674
Leu Tyr Ser Leu Val Phe Ile Phe Gly Phe Val Gly Asn Met Leu Val
    50                  55                  60 gtc ctc atc tta ata aac tgc aaa aag ctg aag tgc ttg act gac att     722
Val Leu Ile Leu Ile Asn Cys Lys Lys Leu Lys Cys Leu Thr Asp Ile
65                  70                  75 tac ctg ctc aac ctg gcc atc tct gat ctg ctt ttt ctt att act ctc     770
Tyr Leu Leu Asn Leu Ala Ile Ser Asp Leu Leu Phe Leu Ile Thr Leu
80                  85                  90                  95 cca ttg tgg gct cac tct gct gca aat gag tgg gtc ttt ggg aat gca     818
Pro Leu Trp Ala His Ser Ala Ala Asn Glu Trp Val Phe Gly Asn Ala
                100                 105                 110 atg tgc aaa tta ttc aca ggg ctg tat cac atc ggt tat ttt ggc gga     866
Met Cys Lys Leu Phe Thr Gly Leu Tyr His Ile Gly Tyr Phe Gly Gly
        115                 120                 125 atc ttc ttc atc atc ctc ctg aca atc gat aga tac ctg gct att gtc     914
Ile Phe Phe Ile Ile Leu Leu Thr Ile Asp Arg Tyr Leu Ala Ile Val
    130                 135                 140 cat gct gtg ttt gct tta aaa gcc agg acg gtc acc ttt ggg gtg gtg     962
His Ala Val Phe Ala Leu Lys Ala Arg Thr Val Thr Phe Gly Val Val
145                 150                 155 aca agt gtg atc acc tgg ttg gtg gct gtg ttt gct tct gtc cca gga    1010
Thr Ser Val Ile Thr Trp Leu Val Ala Val Phe Ala Ser Val Pro Gly
160                 165                 170                 175 atc atc ttt act aaa tgc cag aaa gaa gat tct gtt tat gtc tgt ggc    1058
Ile Ile Phe Thr Lys Cys Gln Lys Glu Asp Ser Val Tyr Val Cys Gly

|                      |      |
|----------------------|------|
| cct tat ttt cca cga gga tgg aat aat ttc cac aca ata atg agg aac<br>Pro Tyr Phe Pro Arg Gly Trp Asn Asn Phe His Thr Ile Met Arg Asn<br>         195               200               205 | 1106 |
| att ttg ggg ctg gtc ctg ccg ctg ctc atc atg gtc atc tgc tac tcg<br>Ile Leu Gly Leu Val Leu Pro Leu Leu Ile Met Val Ile Cys Tyr Ser<br>    210               215               220 | 1154 |
| gga atc ctg aaa acc ctg ctt cgg tgt cga aac gag aag aag agg cat<br>Gly Ile Leu Lys Thr Leu Leu Arg Cys Arg Asn Glu Lys Lys Arg His<br>225                230               235 | 1202 |
| agg gca gtg aga gtc atc ttc acc atc atg att gtt tac ttt ctc ttc<br>Arg Ala Val Arg Val Ile Phe Thr Ile Met Ile Val Tyr Phe Leu Phe<br>240                245               250               255 | 1250 |
| tgg act ccc tat aat att gtc att ctc ctg aac acc ttc cag gaa ttc<br>Trp Thr Pro Tyr Asn Ile Val Ile Leu Leu Asn Thr Phe Gln Glu Phe<br>                          260               265               270 | 1298 |
| ttc ggc ctg agt aac tgt gaa agc acc agt caa ctg gac caa gcc acg<br>Phe Gly Leu Ser Asn Cys Glu Ser Thr Ser Gln Leu Asp Gln Ala Thr<br>         275               280               285 | 1346 |
| cag gtg aca gag act ctt ggg atg act cac tgc tgc atc aat ccc atc<br>Gln Val Thr Glu Thr Leu Gly Met Thr His Cys Cys Ile Asn Pro Ile<br>             290               295               300 | 1394 |
| atc tat gcc ttc gtt ggg gag aag ttc aga agg tat ctc tcg gtg ttc<br>Ile Tyr Ala Phe Val Gly Glu Lys Phe Arg Arg Tyr Leu Ser Val Phe<br>305                310               315 | 1442 |
| ttc cga aag cac atc acc aag cgc ttc tgc aaa caa tgt cca gtt ttc<br>Phe Arg Lys His Ile Thr Lys Arg Phe Cys Lys Gln Cys Pro Val Phe<br>320                325               330               335 | 1490 |
| tac agg gag aca gtg gat gga gtg act tca aca aac acg cct tcc act<br>Tyr Arg Glu Thr Val Asp Gly Val Thr Ser Thr Asn Thr Pro Ser Thr<br>             340               345               350 | 1538 |
| ggg gag cag gaa gtc tcg gct ggt tta taa aacgaggagc agtttgattg<br>Gly Glu Gln Glu Val Ser Ala Gly Leu<br>         355               360 | 1588 |
| ttgtttataa agggagataa caatctgtat ataacaacaa acttcaaggg tttgttgaac | 1648 |
| aatagaaacc tgtaaagcag gtgcccagga acctcagggc tgtgtgtact aatacagact | 1708 |
| atgtcaccca atgcatatcc aacatgtgct cagggaataa tccagaaaaa ctgtgggtag | 1768 |
| agactttgac tctccagaaa gctcatctca gctcctgaaa aatgcctcat taccttgtgc | 1828 |
| taatcctctt tttctagtct tcataatttc ttcactcaat ctctgattct gtcaatgtct | 1888 |
| tgaaatcaag ggccagctgg aggtgaagaa gagaatgtga caggcacaga tgaatgggag | 1948 |
| tgagggatag tggggtcagg gctgagagga gaaggaggga gacatgagca tggctgagcc | 2008 |
| tggacaaaga caaaggtgag caaagggctc acgcattcag ccaggagatg atactggtcc | 2068 |
| ttagccccat ctgccacgtg tatttaacct tgaagggttc accaggtcag ggagagtttg | 2128 |
| ggaactgcaa taacctggga gttttggtgg agtccgatga ttctcttttg cataagtgca | 2188 |
| tgacatattt ttgctttatt acagtttatc tatggcaccc atgcaccttaa catttgaaat | 2248 |
| ctatgaaata tcatgctcca ttgttcagat gcttcttagg ccacatcccc ctgtctaaaa | 2308 |
| attcagaaaa tttttgttta taaaaga | 2335 |

<210> SEQ ID NO 6
<211> LENGTH: 360
<212> TYPE: PRT
<213> ORGANISM: Homo sapiens

<400> SEQUENCE: 6

```
Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
            20                  25                  30

His Lys Phe Asp Val Lys Gln Ile Gly Ala Gln Leu Leu Pro Pro Leu
        35                  40                  45

Tyr Ser Leu Val Phe Ile Phe Gly Phe Val Gly Asn Met Leu Val Val
    50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
    130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
        180                 185                 190

Tyr Phe Pro Arg Gly Trp Asn Asn Phe His Thr Ile Met Arg Asn Ile
    195                 200                 205

Leu Gly Leu Val Leu Pro Leu Leu Ile Met Val Ile Cys Tyr Ser Gly
            210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
        260                 265                 270

Gly Leu Ser Asn Cys Glu Ser Thr Ser Gln Leu Asp Gln Ala Thr Gln
    275                 280                 285

Val Thr Glu Thr Leu Gly Met Thr His Cys Cys Ile Asn Pro Ile Ile
            290                 295                 300

Tyr Ala Phe Val Gly Glu Lys Phe Arg Arg Tyr Leu Ser Val Phe Phe
305                 310                 315                 320

Arg Lys His Ile Thr Lys Arg Phe Cys Lys Gln Cys Pro Val Phe Tyr
                325                 330                 335

Arg Glu Thr Val Asp Gly Val Thr Ser Thr Asn Thr Pro Ser Thr Gly
        340                 345                 350

Glu Gln Glu Val Ser Ala Gly Leu
    355                 360

<210> SEQ ID NO 7
<211> LENGTH: 3686
<212> TYPE: DNA
<213> ORGANISM: Homo sapiens
<220> FEATURE:
<221> NAME/KEY: CDS
<222> LOCATION: (358)..(1416)
```

<400> SEQUENCE: 7

```
cttcagatag attatatctg gagtgaagaa tcctgccacc tatgtatctg gcatagtatt      60
ctgtgtagtg ggatgagcag agaacaaaaa caaaataatc cagtgagaaa agcccgtaaa     120
taaaccttca gaccagagat ctattctcta gcttatttta agctcaactt aaaaagaaga     180
actgttctct gattctttc gccttcaata cacttaatga tttaactcca ccctccttca     240
aaagaaacag catttcctac ttttatactg tctatatgat tgatttgcac agctcatctg     300
gccagaagag ctgagacatc cgttccccta caagaaactc tccccgggtg aacaag        357 atg gat tat caa gtg tca agt cca atc tat gac atc aat tat tat aca      405
Met Asp Tyr Gln Val Ser Ser Pro Ile Tyr Asp Ile Asn Tyr Tyr Thr
1               5                   10                  15 tcg gag ccc tgc caa aaa atc aat gtg aag caa atc gca gcc cgc ctc      453
Ser Glu Pro Cys Gln Lys Ile Asn Val Lys Gln Ile Ala Ala Arg Leu
            20                  25                  30 ctg cct ccg ctc tac tca ctg gtg ttc atc ttt ggt ttt gtg ggc aac      501
Leu Pro Pro Leu Tyr Ser Leu Val Phe Ile Phe Gly Phe Val Gly Asn
        35                  40                  45 atg ctg gtc atc ctc atc ctg ata aac tgc aaa agg ctg aag agc atg      549
Met Leu Val Ile Leu Ile Leu Ile Asn Cys Lys Arg Leu Lys Ser Met
    50                  55                  60 act gac atc tac ctg ctc aac ctg gcc atc tct gac ctg ttt ttc ctt      597
Thr Asp Ile Tyr Leu Leu Asn Leu Ala Ile Ser Asp Leu Phe Phe Leu
65                  70                  75                  80 ctt act gtc ccc ttc tgg gct cac tat gct gcc gcc cag tgg gac ttt      645
Leu Thr Val Pro Phe Trp Ala His Tyr Ala Ala Ala Gln Trp Asp Phe
                85                  90                  95 gga aat aca atg tgt caa ctc ttg aca ggg ctc tat ttt ata ggc ttc      693
Gly Asn Thr Met Cys Gln Leu Leu Thr Gly Leu Tyr Phe Ile Gly Phe
            100                 105                 110 ttc tct gga atc ttc ttc atc atc ctc ctg aca atc gat agg tac ctg      741
Phe Ser Gly Ile Phe Phe Ile Ile Leu Leu Thr Ile Asp Arg Tyr Leu
        115                 120                 125 gct gtc gtc cat gct gtg ttt gct tta aaa gcc agg acg gtc acc ttt      789
Ala Val Val His Ala Val Phe Ala Leu Lys Ala Arg Thr Val Thr Phe
    130                 135                 140 ggg gtg gtg aca agt gtg atc act tgg gtg gtg gct gtg ttt gcg tct      837
Gly Val Val Thr Ser Val Ile Thr Trp Val Val Ala Val Phe Ala Ser
145                 150                 155                 160 ctc cca gga atc atc ttt acc aga tct caa aaa gaa ggt ctt cat tac      885
Leu Pro Gly Ile Ile Phe Thr Arg Ser Gln Lys Glu Gly Leu His Tyr
                165                 170                 175 acc tgc agc tct cat ttt cca tac agt cag tat caa ttc tgg aag aat      933
Thr Cys Ser Ser His Phe Pro Tyr Ser Gln Tyr Gln Phe Trp Lys Asn
            180                 185                 190 ttc cag aca tta aag ata gtc atc ttg ggg ctg gtc ctg ccg ctg ctt      981
Phe Gln Thr Leu Lys Ile Val Ile Leu Gly Leu Val Leu Pro Leu Leu
        195                 200                 205 gtc atg gtc atc tgc tac tcg gga atc cta aaa act ctg ctt cgg tgt     1029
Val Met Val Ile Cys Tyr Ser Gly Ile Leu Lys Thr Leu Leu Arg Cys
    210                 215                 220 cga aat gag aag aag agg cac agg gct gtg agg ctt atc ttc acc atc     1077
Arg Asn Glu Lys Lys Arg His Arg Ala Val Arg Leu Ile Phe Thr Ile
225                 230                 235                 240 atg att gtt tat ttt ctc ttc tgg gct ccc tac aac att gtc ctt ctc     1125
Met Ile Val Tyr Phe Leu Phe Trp Ala Pro Tyr Asn Ile Val Leu Leu
                245                 250                 255 ctg aac acc ttc cag gaa ttc ttt ggc ctg aat aat tgc agt agc tct     1173
```

```
Leu Asn Thr Phe Gln Glu Phe Phe Gly Leu Asn Asn Cys Ser Ser Ser
            260                 265                 270 aac agg ttg gac caa gct atg cag gtg aca gag act ctt ggg atg acg      1221
Asn Arg Leu Asp Gln Ala Met Gln Val Thr Glu Thr Leu Gly Met Thr
        275                 280                 285 cac tgc tgc atc aac ccc atc atc tat gcc ttt gtc ggg gag aag ttc      1269
His Cys Cys Ile Asn Pro Ile Ile Tyr Ala Phe Val Gly Glu Lys Phe
        290                 295                 300 aga aac tac ctc tta gtc ttc ttc caa aag cac att gcc aaa cgc ttc      1317
Arg Asn Tyr Leu Leu Val Phe Phe Gln Lys His Ile Ala Lys Arg Phe
305                 310                 315                 320 tgc aaa tgc tgt tct att ttc cag caa gag gct ccc gag cga gca agc      1365
Cys Lys Cys Cys Ser Ile Phe Gln Gln Glu Ala Pro Glu Arg Ala Ser
                325                 330                 335 tca gtt tac acc cga tcc act ggg gag cag gaa ata tct gtg ggc ttg      1413
Ser Val Tyr Thr Arg Ser Thr Gly Glu Gln Glu Ile Ser Val Gly Leu
            340                 345                 350
``` tga cacggactca agtgggctgg tgacccagtc agagttgtgc acatggctta           1466
gttttcatac acagcctggg ctggggtgg ggtgggagag gtctttttta aaaggaagtt    1526
actgttatag agggtctaag attcatccat ttatttggca tctgtttaaa gtagattaga    1586
tcttttaagc ccatcaatta tagaaagcca aatcaaaata tgttgatgaa aaatagcaac    1646 cttttatct ccccttcaca tgcatcaagt tattgacaaa ctctcccttc actccgaaag     1706
ttccttatgt atatttaaaa gaaagcctca gagaattgct gattcttgag tttagtgatc    1766
tgaacagaaa taccaaaatt atttcagaaa tgtacaactt tttacctagt acaaggcaac    1826
atataggttg taaatgtgtt taaaacaggt ctttgtcttg ctatggggag aaaagacatg    1886
aatatgatta gtaaagaaat gacacttttc atgtgtgatt tcccctccaa ggtatggtta    1946
ataagtttca ctgacttaga accaggcgag agacttgtgg cctgggagag ctggggaagc    2006
ttcttaaatg agaaggaatt tgagttggat catctattgc tggcaaagac agaagcctca    2066
ctgcaagcac tgcatgggca agcttggctg tagaaggaga cagagctggt tgggaagaca    2126
tggggaggaa ggacaaggct agatcatgaa gaaccttgac ggcattgctc cgtctaagtc    2186
atgagctgag cagggagatc ctggttgtgt ttgcagaagg tttactctgt ggccaaagga    2246
gggtcaggaa ggatgagcat ttagggcaag gagaccacca acagccctca ggtcagggtg    2306
aggatggcct ctgctaagct caaggcgtga ggatgggaag gagggaggta ttcgtaagga    2366
tgggaaggag ggaggtattc gtgcagcata tgaggatgca gagtcagcag aactggggtg    2426
gatttgggtt ggaagtgagg gtcagagagg agtcagagag aatccctagt cttcaagcag    2486
attggagaaa cccttgaaaa gacatcaagc acagaaggag gaggaggagg tttaggtcaa    2546
gaagaagatg gattggtgta aaaggatggg tctggtttgc agagcttgaa cacagtctca    2606
cccagactcc aggctgtctt tcactgaatg cttctgactt catagatttc cttcccatcc    2666
cagctgaaat actgagggggt ctccaggagg agactagatt tatgaataca cgaggtatga   2726
ggtctaggaa catacttcag ctcacacatg agatctaggt gaggattgat tacctagtag    2786
tcatttcatg ggttgttggg aggattctat gaggcaacca caggcagcat ttagcacata    2846
ctacacattc aataagcatc aaactcttag ttactcattc agggatagca ctgagcaaag    2906
cattgagcaa agggggtccca tagaggtgag ggaagcctga aaaactaaga tgctgcctgc   2966
ccagtgcaca caagtgtagg tatcattttc tgcatttaac cgtcaatagg caaagggggg    3026
aagggacata ttcatttgga aataagctgc cttgagcctt aaaacccaca aaagtacaat    3086

-continued

```
ttaccagcct ccgtatttca gactgaatgg gggtgggggg ggcgccttag gtacttattc    3146
cagatgcctt ctccagacaa accagaagca acagaaaaaa tcgtctctcc ctcccttga    3206 aatgaatata cccttagtg tttgggtata ttcatttcaa agggagagag agaggttttt    3266
ttctgttctg tctcatatga ttgtgcacat acttgagact gttttgaatt tgggggatgg    3326
ctaaaaccat catagtacag gtaaggtgag ggaatagtaa gtggtgagaa ctactcaggg    3386
aatgaaggtg tcagaataat aagaggtgct actgactttc tcagcctctg aatatgaacg    3446
gtgagcattg tggctgtcag caggaagcaa cgaagggaaa tgtctttcct tttgctctta    3506
agttgtggag agtgcaacag tagcatagga ccctaccctc tgggccaagt caaagacatt    3566
ctgacatctt agtatttgca tattcttatg tatgtgaaag ttacaaattg cttgaaagaa    3626
aatatgcatc taataaaaaa caccttctaa aataaaaaaa aaaaaaaaa aaaaaaaaa     3686
```

```
<210> SEQ ID NO 8
<211> LENGTH: 352
<212> TYPE: PRT
<213> ORGANISM: Homo sapiens

<400> SEQUENCE: 8
```

```
Met Asp Tyr Gln Val Ser Ser Pro Ile Tyr Asp Ile Asn Tyr Tyr Thr
 1               5                  10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
           100                 105                 110

Phe Ser Gly Ile Phe Phe Ile Ile Leu Leu Thr Ile Asp Arg Tyr Leu
       115                 120                 125

Ala Val Val His Ala Val Phe Ala Leu Lys Ala Arg Thr Val Thr Phe
   130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
           180                 185                 190

Phe Gln Thr Leu Lys Ile Val Ile Leu Gly Leu Val Leu Pro Leu Leu
       195                 200                 205

Val Met Val Ile Cys Tyr Ser Gly Ile Leu Lys Thr Leu Leu Arg Cys
   210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
           260                 265                 270
```

-continued

```
Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350
```

AGENT FOR CONTROLLING CELLS CONSTITUTING CANCER MICROENVIRONMENT OR INFLAMMATORY MICROENVIRONMENT

TECHNICAL FIELD

The present invention relates to a novel FROUNT protein inhibitor, and control of cells constituting a cancer microenvironment or inflammatory microenvironment using the inhibitor.

BACKGROUND ART

FROUNT protein is a cytoplasmic protein that binds to the intracellular C-terminal regions of chemokine receptors CCR2 and CCR5, and positively controls migration signals of macrophages and the like (Patent Document 1, Non-patent Documents 1 and 2). This protein is a novel molecule discovered by the group of the present inventors.

Both CCR2 and CCR5 are known to be involved in cancers and inflammatory diseases, and development of inhibitors for CCR2 and CCR5 has been attempted worldwide aiming at discovery of novel therapeutic agents for these diseases. However, none of these attempts has been successful. The targets of the existing approaches have been the binding between a chemokine CCL2 and a receptor CCR2, the binding between chemokines CCL3 to 5 and a receptor CCR5, and the signal transduction system by PI3K and the like functioning downstream of the receptors. Inhibition of binding of FROUNT protein to the chemokine receptors CCR2 and CCR5 has been expected as a novel drug discovery target (Non-patent Documents 3 and 4).

The present inventors have reported an inhibitor comprising as an effective component a compound represented by the following formula or a salt thereof, as an inhibitor that inhibits interaction between CCR2 or CCR5 and FROUNT protein (Patent Document 1).

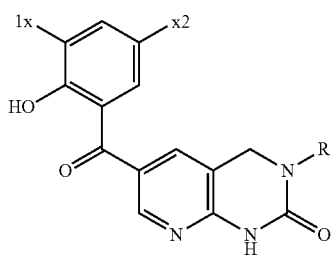

(wherein x1 and x2 are the same or different halogens, and R is a lower alkyl.)

Disulfiram has an aldehyde dehydrogenase-inhibiting activity, and inhibits ethanol metabolism in the liver to cause accumulation of acetaldehyde, which is responsible for sickness caused by drinking, in the body. Thus, after taking of disulfiram, symptoms of sickness caused by drinking occur even with a small amount of alcohol. By utilization of this action, disulfiram is used as an anti-alcoholism drug for treatment of chronic alcoholism.

Besides the above-described action, disulfiram is reported to have an action to inhibit the proliferation of cancer cells by induction of their apoptosis (for example, Non-patent Documents 5 to 7). Disulfiram is also reported to have an action to kill hepatic cancer stem cells (Patent Document 2). All these reports are reports on actions for killing cancer cells or cancer stem cells per se. Because of such direct actions on cancer cells, clinical trials targeting cancer are being partially carried out (Non-patent Document 8). However, actions of disulfiram on microenvironment-constituting cells such as immune cells, fibroblasts, vascular endothelial cells and the like present in the vicinity of cancer cells have not been known at all. Actions of disulfiram on inflammatory microenvironments in diseases in which inflammation is involved have not also been known at all.

PRIOR ART DOCUMENT(S)

Patent Document(s)

Patent Document 1: JP 5424960 B
Patent Document 2: JP 2013-100268 A

Non-Patent Document(S)

Non-patent Document 1: Nat. Immunol. Vol. 6, pp. 827-835 (2005)
Non-patent Document 2: J Immunol. Vol. 183, pp. 6387-6394 (2009)
Non-patent Document 3: Endocrinology, Diabetology & Metabolism, 35(6): 500-507 (2012)
Non-patent Document 4: Gan Kiban Seibutsugaku—Kakushinteki Seeds Ikusei Ni Mukete—(Cancer Basic Biology—Towards Cultivation of Innovative Seeds—), Nanzando Co., Ltd., 2013, p. 130-136
Non-patent Document 5: Cancer Research, Vol. 66, pp. 10425-10433 (2006)
Non-patent Document 6: Clinical Cancer Research, Vol. 15, pp. 6070-6078 (2009)
Non-patent Document 7: Molecular Cancer Therapeutics, Vol. 1, pp. 197-204 (2002)
Non-patent Document 8: The Oncologist, Vol. 20, pp. 366-367 (2015)

SUMMARY OF THE INVENTION

Problems to be Solved by the Invention

In treatment of cancers and treatment of diseases in which inflammation is involved, it is expected that not only agents that directly act on target cells that cause the diseased state, but also appropriate control of cells constituting the cancer lesion or cells constituting the inflammatory lesion, may lead to a cure. An object of the present invention is to provide a substance whose effect on cancers and inflammatory diseases is higher than those of known FROUNT inhibitors, and which is therefore more useful as a pharmaceutical, and to provide novel means for providing such a substance.

Means for Solving the Problems

As a result of intensive screening of a library containing about 130,000 kinds of low molecular compounds, the present inventors newly identified substances having an activity that inhibits FROUNT protein, and discovered that the substances inhibit excessive hyperplasia and accumulation of microenvironment-constituting cells present in the vicinity of cancer cells, especially accumulation of macrophages in the lesion, resulting in inhibition of the proliferation and metastasis of cancer cells, and that the substances also have an action to inhibit accumulation of macrophages in inflammatory sites and migration of leukemia cells, so that the substances are also effective for inflammatory diseases and humoral cancers. The present inventors further identified the spatial structure of the binding region complex of FROUNT protein and CCR2, and obtained a spatial structure information that is useful for development of a stronger FROUNT protein inhibitor, thereby completing the present invention.

That is, the present invention provides an agent for inhibiting macrophages comprising as an effective component any of the following (1) to (3):

(1) disulfiram, diethyldithiocarbamate, or a metal complex of diethyldithiocarbamate;
(2) a pharmaceutically acceptable salt of (1);
(3) a solvate of (1) or (2).

The present invention also provides an agent for controlling cells constituting a cancer microenvironment or inflammatory microenvironment, said agent comprising as an effective component any of the above-described (1) to (3). The present invention further provides an agent for inhibiting interaction between CCR2B or CCR5 and FROUNT protein, said agent comprising as an effective component any of the above-described (1) to (3). The present invention still further provides an agent for enhancing anticancer activity of an anticancer drug, said agent comprising as an effective component any of the above-described (1) to (3). The present invention still further provides a method for inhibiting macrophages, a method for inhibiting cells constituting a cancer microenvironment or inflammatory microenvironment, a method for inhibiting interaction between CCR2B or CCR5 and FROUNT protein, and a method for enhancing anticancer activity of an anticancer drug, said methods comprising administering an effective amount of any of the above-described (1) to (3) to a subject in need thereof.

The present invention still further provides a method for identifying a disulfiram derivative having an improved ability to inhibit interaction between FROUNT protein and CCR2B or CCR5, said method comprising the steps of: incubating a FROUNT protein fragment containing the region of the 564th to 600th amino acids of FROUNT protein, and a CCR2B fragment containing the region of the 312th to 323rd amino acids in the amino acid sequence of CCR2B shown in SEQ ID NO:6 or a CCR5 fragment containing the region of the 304th to 315th amino acids in the amino acid sequence of CCR5 shown in SEQ ID NO:8, together with a disulfiram derivative library; and selecting a disulfiram derivative having a higher activity to inhibit binding of the FROUNT protein fragment to the CCR2B fragment or CCR5 fragment compared to disulfiram. The present invention still further provides a method for producing an agent for inhibiting interaction between FROUNT protein and CCR2B or CCR5, said method comprising the steps of: identifying a disulfiram derivative having an improved ability to inhibit interaction between FROUNT protein and CCR2B or CCR5 by the method of the present invention described above; and producing the identified disulfiram derivative. The present invention still further provides a method for identifying a compound having an improved ability to inhibit interaction between FROUNT protein and CCR2B or CCR5, said method comprising the steps of: incubating a FROUNT protein fragment containing the region of the 564th to 600th amino acids of FROUNT protein, and a CCR2B fragment containing the region of the 312th to 323rd amino acids in the amino acid sequence of CCR2B shown in SEQ ID NO:6 or a CCR5 fragment containing the region of the 304th to 315th amino acids in the amino acid sequence of CCR5 shown in SEQ ID NO:8, together with a library of derivatives of a candidate FROUNT inhibitor compound; and selecting a derivative having a higher activity to inhibit binding of the FROUNT protein fragment to the CCR2B fragment or the CCR5 fragment compared to the original candidate compound. The present invention still further provides a method for identifying a substance that inhibits interaction between FROUNT protein and CCR2B or CCR5, said method comprising: constructing a binding pocket structure of FROUNT protein constituted by amino acid residues including at least one selected from the group consisting of M564, T565, I568, A569, M575, L578, and L600 in silico using at least part of the atomic coordinates of FROUNT protein; calculating the strength of binding of the binding pocket structure to a compound library; and selecting a compound that forms a stable complex with FROUNT protein. The present invention still further provides a method for designing a substance that inhibits interaction between FROUNT protein and CCR2B or CCR5, said method comprising: allowing a candidate compound to bind in silico to a binding pocket structure in which FROUNT protein binds to CCR2B or CCR5; and calculating the strength of the binding.

Effect of the Invention

By the present invention, a novel agent for inhibiting microenvironment-constituting cells including macrophages was provided. The agent of the present invention does not kill cancer cells per se, but inhibits excessive hyperplasia and accumulation of microenvironment-constituting cells present in the vicinity of cancer cells, especially accumulation of macrophages in the lesion, resulting in inhibition of the proliferation and metastasis of cancer cells. The agent of the present invention has an action to inhibit accumulation of macrophages in inflammatory sites and migration of leukemia cells, so that the agent is also effective for inflammatory diseases and humoral cancers. Based on the microenvironment controlling action, the agent is expected to be widely applied to various types of cancers and other inflammatory diseases. By use of the agent of the present invention in combination with a known anticancer drug, the anticancer effect of the anticancer drug can be increased. Therefore, the agent of the present invention is expected to be widely applied to patients in whom use of an anticancer drug alone was not effective. It is also expected that side effects and the medical cost can be reduced thanks to reduction of the dose or dosage of an anticancer drug. Disulfiram has been conventionally practically used as an anti-alcoholism drug for treatment of patients with chronic alcoholism. By identifying a disulfiram derivative having a lower aldehyde dehydrogenase-inhibiting activity and a higher FROUNT-inhibiting activity among derivatives prepared by structural modification of disulfiram, a compound having a reduced side effect and an increased pharmacological effect can also be provided.

MODE FOR CARRYING OUT THE INVENTION

Figure 1:
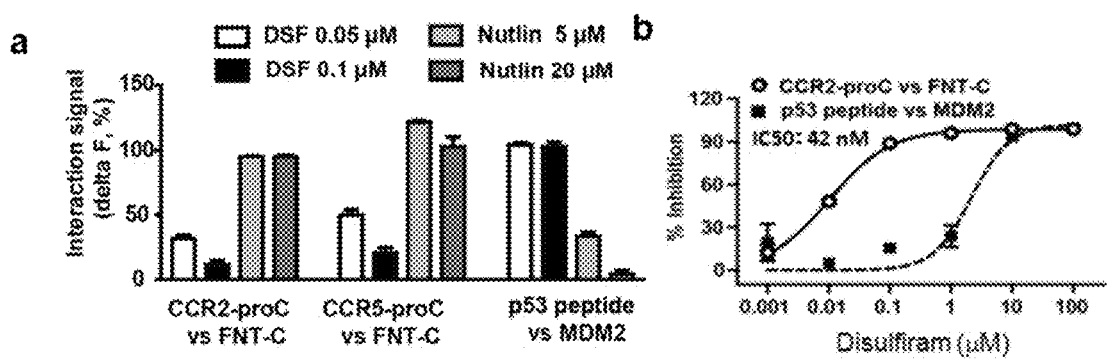
FIG. 1(a) shows the result of a binding inhibition assay according to the HTRF method. Disulfiram selectively inhibited the FROUNT-CCR2 interaction and the FROUNT-CCR5 interaction, but did not inhibit the p53-MDM2 interaction.
FIG. 1(b) is a graph showing patterns of inhibition of the CCR2-FROUNT interaction and the p53-MDM2 interaction by disulfiram.

In the present invention, any of the followings is used as an effective component.

(1) Disulfiram, diethyldithiocarbamate, or a metal complex of diethyldithiocarbamate.
(2) A pharmaceutically acceptable salt of (1).
(3) A solvate of (1) or (2).

The present inventors revealed that disulfiram has an action to inhibit binding (interaction) of FROUNT protein to CCR2B and CCR5, and that disulfiram can therefore be used as a FROUNT inhibitor. Disulfiram is metabolized in the body to generate diethyldithiocarbamate. It has been shown that compounds from which diethyldithiocarbamate is generated have a FROUNT-inhibiting action and a cell migration-inhibiting activity and the like produced from the action.

FROUNT protein is a protein that was identified by the present inventors. Its sequence information has been deposited in an NCBI database GenBank under Accession Nos. AF498261 and NM_024844. The sequences shown in SEQ ID NOs:1 and 2 in SEQUENCE LISTING are cDNA of the FROUNT gene deposited under AF498261 and the amino acid sequence of the FROUNT protein encoded thereby.

There are two isoforms in CCR2, that is, CCR2A and CCR2B, having different C-terminal regions. The major isoform is CCR2B. It has been shown that FROUNT protein binds to the membrane-proximal region in the intracellular C-terminal region of CCR2B and CCR5 (EKFRRYLSVF-FRKHIT (SEQ ID NO:3) in CCR2B, and EKFRNYLL-VFFQKHIA (SEQ ID NO:4) in CCR5) (Biochem. J. (2014) 457, 313-322). In the present description, when the term "CCR2" is simply mentioned, it means CCR2B unless the context clearly indicates otherwise. SEQ ID NOs:5 and 6 show CCR2B sequences (GenBank NM_001123396.1), and SEQ ID NOs:7 and 8 show CCR5 sequences (GenBank NM_000579.3).

Disulfiram controls cells constituting the microenvironments of lesions in cancers and inflammatory diseases by inhibition of FROUNT protein. Disulfiram can therefore be used as an agent for controlling cells constituting the microenvironments of lesions in these diseases. In the present invention, the terms "inhibition of FROUNT protein" and "FROUNT inhibition" mean inhibition of interaction between FROUNT and CCR2 or CCR5.

The microenvironment means an environment in a body in which cells derived from two or more kinds of tissues coexist. Examples of the cells constituting the microenvironments in lesions of cancers and inflammatory diseases (which may also be abbreviated as "microenvironment-constituting cells" in the present description) include immune cells (macrophages, dendritic cells, T cells, B cells, and the like), fibroblasts, vascular endothelial cells, pericytes, inflammatory cells (eosinophils, mast cells, neutrophils, basophils, and the like), and somatic stem cells. In the present invention, the term "cancer microenvironment-constituting cells" means microenvironment-constituting cells other than cancer cells.

The control of microenvironment-constituting cells mainly refers to inhibition of these cells. In cancer microenvironments and inflammatory microenvironments, the cells constituting the environments show abnormal infiltration from the outside and abnormal accumulation in these environments, as well as abnormal hyperplasia in the environments. The control of microenvironment-constituting cell means inhibition of such abnormal infiltration and hyperplasia. By controlling cells that constitute the microenvironments in lesions of cancers and inflammatory diseases, these diseases can be treated or prevented, or their progression, exacerbation, metastasis, or recurrence can be prevented.

Control of microenvironment-constituting cells may be, for example, inhibition of macrophages. Examples of the inhibition of macrophages include inhibition of migration or tissue infiltration of macrophages. It is known that excessive accumulation and infiltration of immune cells such as macrophages are involved in development and exacerbation of a number of cancers and inflammatory diseases, and in induction of metastasis and the like in cancers. Thus, by inhibition of macrophage infiltration in the microenvironments in lesions of cancers and inflammatory diseases, treatment, prophylaxis, prevention of progression, prevention of exacerbation, prevention of metastasis, prevention of recurrence, and the like of these diseases become possible. However, the action to control microenvironment-constituting cells by the agent of the present invention is not limited to inhibition of macrophages.

FROUNT protein, which binds to the intracellular C-terminal region of CCR2 and CCR5 to cause the downstream signal transduction, is inhibited by disulfiram. Thus, the agent of the present invention is effective for cancers and inflammatory diseases in which CCR2 or CCR5, or their ligand (CCL2 or CCL5) is known to be involved, or cancers and inflammatory diseases for which an inhibitor of these molecules (chemokine inhibitor) is known to be effective. The agent of the present invention is also effective for cancers and inflammatory diseases with microenvironments in which FROUNT is expressed, and the higher the expression level of FROUNT, the higher the effect is expected to be.

Examples of the cancers to be targeted include both solid cancers and humoral cancers, and also include both primary cancers and metastatic cancers. Specific example of the cancers include, but are not limited to, lung cancer, melanoma, gastric cancer, colon cancer, breast cancer, liver cancer, pancreatic cancer, uterine cancer, esophageal cancer, prostate cancer, malignant lymphoma, and leukemia. Known examples of cancers in which CCR2 is involved include melanoma, breast cancer, prostate cancer, lung cancer, myeloma, and brain tumor, and known examples of cancers in which CCR5 is involved include breast cancer, prostate cancer, lung cancer, pancreatic cancer, and myeloma (Scholten D J, et al., Br J Pharmacol, 165: 1617-1643, 2012). Examples of anticancer drugs in the field of chemokines that have advanced to clinical trials include an anticancer drug for metastatic castration-resistant prostate cancer targeting CCL2, an anticancer drug for non-small cell lung cancer targeting CCL5, an anticancer drug for metastatic cancers targeting CCR2, and an anticancer drug for advanced colon cancer targeting CCR5 (Gan Kiban Seibutsugaku—Kakushinteki Seeds Ikusei Ni Mukete—(Cancer Basic Biology—Towards Cultivation of Innovative Seeds—), Nanzando Co., Ltd., 2013, p. 130-136). These cancers are preferred specific examples to be targeted by the present invention.

The inflammatory diseases to be targeted in the present invention are typically chronic inflammatory diseases. Specific examples of the inflammatory diseases include, but are not limited to, rheumatoid arthritis, fibrosis, peritonitis, multiple sclerosis, arteriosclerosis, diabetes, asthma, Alzheimer's disease, psoriasis, atopic diseases, ischemic heart diseases, and cerebrovascular diseases. Examples of inflammatory diseases in which at least one of CCR2, CCR5, CCL2, and CCL5 is known to be involved include arteriosclerosis, multiple sclerosis, rheumatoid arthritis, psoriasis, type 2 diabetes, inflammatory bowel disease, chronic hepatitis, nephritis, graft-versus-host disease, chronic obstructive lung disease, asthma, and acquired immune deficiency syndrome (Scholten D J et al., Br J Pharmacol, 165: 1617-1643, 2012; Clinical Immunology & Allergology, 59(3): 386-391, 2013). Other examples of inflammatory diseases in which at least one of CCR2, CCR5, CCL2, and CCL5, or FROUNT is involved include various fibrotic diseases such as pulmonary fibrosis and hepatic fibrosis; peritonitis; and allergic airway hyperresponsiveness (Nippon Rinsho, vol. 70, extra edition 8, 365-371, 2012; and the Examples described below). These inflammatory diseases are preferred specific examples to be targeted by the present invention.

The metal complex of diethyldithiocarbamate may be a complex of any metal. Specific examples of the metal complex include, but are not limited to, zinc complex, iron (II) complex, iron (III) complex, copper complex, and platinum complex.

Disulfiram, diethyldithiocarbamate, or the metal complex of diethyldithiocarbamate may also be used in the form of a pharmaceutically acceptable salt. The salt may be an acid addition salt or a base addition salt. Specific examples of the acid addition salt include inorganic acid salts such as hydrochloric acid salt, hydrobromic acid salt, sulfuric acid salt, hydroiodic acid salt, nitric acid salt, and phosphoric acid salt; and organic acid salts such as citric acid salt, oxalic acid salt, acetic acid salt, formic acid salt, propionic acid salt, benzoic acid salt, trifluoroacetic acid salt, maleic acid salt, tartaric acid salt, methanesulfonic acid salt, benzenesulfonic acid salt, and para-toluenesulfonic acid salt. Specific examples of the base addition salt include inorganic base salts such as sodium salt, potassium salt, calcium salt, magnesium salt, and ammonium salt; and organic base salts such as triethylammonium salt, triethanolammonium salt, pyridinium salt, and diisopropylammonium salt.

Disulfiram, diethyldithiocarbamate, or the metal complex of diethyldithiocarbamate, or the pharmaceutically acceptable salt thereof may also be used in the form of a solvate. Specific examples of the solvate include, but are not limited to, hydrates and ethanolates. The solvate may be any solvate as long as it is a solvate with a pharmaceutically acceptable solvent.

Disulfiram per se is a known compound, and is conventionally used as an anti-alcoholism drug for treatment of chronic alcoholism. Disulfiram is a prescription medication listed in the Japanese Pharmacopoeia, and its production method is well known. Diethyldithiocarbamate and its metal complexes, and the pharmaceutically acceptable salts and solvates of disulfiram and the like described above can also be produced by methods known in the field of chemical synthesis.

When the agent of the present invention is used as a pharmaceutical, the administration route may be systemic administration or local administration, and may be oral administration or parenteral administration. Examples of the parenteral administration include intramuscular administration, subcutaneous administration, intravenous administration, intraarterial administration, and transdermal administration. The agent may be locally administered in the vicinity of the lesion, or, when it is used for cancer, it may be administered to a regional lymph node in the vicinity of the tumor site.

When the agent of the present invention is prepared as a pharmaceutical, disulfiram, diethyldithiocarbamate, a metal complex of diethyldithiocarbamate, a salt of any of these compounds, or a solvate of any of these compounds or salts thereof may be mixed as appropriate with an additive(s) such as a pharmaceutically acceptable carrier, diluent, and/or vehicle suitable for each administration route, to prepare a formulation. Examples of the formulation include oral preparations such as tablets, capsules, granules, powders, and syrups; and parenteral preparations such as inhalants, injection solutions, suppositories, and solutions. Formulation methods and additives which can be used are well known in the field of pharmaceutical preparations, and any of the methods and the additives may be employed.

Techniques for preparing sustained release formulations are also well known. The agent of the present invention may be provided as a sustained release formulation aiming at stabilization and retention of the blood level of the effective component. The term "sustained release" used herein has the same meaning as controlled release, and also includes delayed release and the like. The techniques for preparing sustained release formulations can be classified into the single-unit type and the multiple-unit type based on the form of the sustained release formulation, or can be classified into the reservoir type, matrix type and the like based on the release control mechanism. Hybrid types, in which a plurality of mechanisms are combined, are also known. When the agent of the present invention is prepared as a sustained release formulation, any of the techniques for preparation of sustained release formulations may be used. A DDS such as liposomes may be used for the preparation. The sustained release formulation may be prepared into any dosage form including a tablet, granule, capsule or the like. Specific examples of the sustained release formulation of disulfiram include the disulfiram formulation described in WO 2012/076897 A1, in which liposomes are used as a DDS, and the solid dispersion tablet of disulfiram described in International Journal of Pharmaceutics 497 (2016) 3-11, in which a polyvinyl acetate-polyvinyl pyrrolidone mixture or hypromellose is used as a sustained release polymer. However, the sustained release formulation of disulfiram is not limited to these specific examples.

The administration amount of the agent of the present invention may be any amount as long as it is effective for treatment of the cancer or inflammatory disease to be targeted. The effective amount is appropriately selected depending on, for example, the size of the lesion, symptoms, severity, the age and/or the body weight of the patient, and/or the like. Although the administration amount of the agent of the present invention is not limited, it may be about 0.001 mg to about 10 g, for example, about 0.1 mg to about 1000 mg, or about 5 mg to about 500 mg, or about 5 mg to 200 mg, in terms of the amount of the effective component per administration to an adult (60 kg body weight). The agent may be administered once or several times per day. During the treatment period, the agent may be administered once, or daily for a period of several days or longer, or may be administered multiple times every several days, every several weeks, or every several months. For example, multiple times (for example, about 2 to 5 times) of administration per day may be carried out everyday during the treatment period. As described in the following Examples, the FROUNT-inhibiting ability of disulfiram is obtained by administering disulfiram in a form which can be degraded into DDC, and is lost in a form of the downstream metabolites. Thus, frequent administration is more preferred than once daily administration at a high dose. However, depending on the performance of the sustained release formulation, the frequency of administration can be reduced.

The patient to which the agent of the present invention is administered is a mammal. Although the mammal is not limited, it is typically human.

The agent of the present invention may be used in combination with at least one of known anticancer drugs and anti-inflammatory drugs. The term "used in combination" means that the agent of the present invention and the at least one anticancer drug or anti-inflammatory drug are administered to a patient simultaneously, sequentially, or separately. The agent and a drug(s) to be used in combination may be provided as separate formulations, or, in cases where they are simultaneously administered, the effective components of the agent and a drug(s) may be contained in a single formulation.

The term "anticancer" includes inhibition of development (initiation, metastasis, or recurrence) of cancer and inhibition of growth of cancer. Accordingly, "anticancer drug" includes therapeutic agents, prophylactic agents, metastasis-inhibiting agents, and recurrence-inhibiting agents for cancer.

The anticancer drug that may be used in combination with the agent of the present invention may be an antibody or an antigen-binding fragment thereof. The antibody is preferably a monoclonal antibody, and, in cases where the subject to which it is administered is human, a human type chimeric antibody, humanized antibody (an antibody prepared by transplanting the CDR region of a non-human-derived antibody to the corresponding region of a human antibody), or human antibody (the same antibody as an antibody produced in the body of human, which is prepared using a non-human animal or a human cell line) is preferably used.

Preferred examples of the anticancer drug that may be used in combination include anticancer drugs targeting immune checkpoints. Immune checkpoints are the immune escape mechanism to prevent the immune system from attacking its own body. Immune checkpoint receptors are present on T cells, and interact with ligands expressed on antigen-presenting cells. T cells recognize an antigen presented on the MHC molecule and are activated to generate an immune reaction, whereas the activation of T cells is controlled by an interaction between immune checkpoint receptor and ligand that occurs in parallel. Immune checkpoint receptors can be divided into inhibitory receptors and co-stimulatory receptors, and the T cell activation and the immune reaction are controlled by a balance between both receptors.

Cancer cells utilize such an immune checkpoint mechanism. By expressing a ligand for an inhibitory immune checkpoint receptor, cancer cells suppress the immune function to escape from attack of cytotoxic T cells. Therefore, inhibition of inhibitory immune checkpoint molecules can prevent cancer cells from utilizing the immune checkpoint mechanism, thereby facilitating killing of cancer cells by $CD8^+$ T cells.

Various kinds of anticancer drugs targeting immune checkpoints have been developed, and their clinical trials and practical use have progressed worldwide. Agents that inhibit inhibitory immune checkpoints are also called immune checkpoint inhibitors, and their practical use has especially progressed among the anticancer drugs targeting immune checkpoints. Specific examples of such immune checkpoint inhibitors include antagonistic anti-PD-1 antibodies and antagonistic anti-CTLA-4 antibodies, as well as anti-PD-L1 antibodies and anti-PD-L2 antibodies that bind to PD-L1 and PD-L2, which are ligands for the receptor PD-1, to inhibit binding of the ligands to the receptor.

However, the anticancer drugs targeting immune checkpoints are not limited to immune checkpoint inhibitors (antagonists against inhibitory immune checkpoint molecules), and agonists against co-stimulatory immune checkpoint molecules may also be used in combination with the agent of the present invention. Administration of an agonist against a co-stimulatory immune checkpoint receptor can enhance the immune reaction, by which killing of cancer cells by $CD8^+$ T cells can also be facilitated. The agent of the present invention, an immune checkpoint inhibitor, and an agonist against a co-stimulatory immune checkpoint molecule may be also used in combination.

In the present invention, the term "immune checkpoint molecule" includes both receptors and ligands that function as an immune checkpoint.

Specific examples of inhibitory immune checkpoint molecules that can be targeted by anticancer drugs targeting immune checkpoints include receptors such as PD-1, CTLA-4, LAG-3, TIM-3, and BTLA; and ligands such as PD-L1 (ligand for PD-1), PD-L2 (ligand for PD-1), CD80 (ligand for CTLA-4), CD86 (ligand for CTLA-4), GAL9 (ligand for TIM-3), and HVEM (ligand for BTLA). Specific examples of co-stimulatory immune checkpoint molecules that can be targeted include receptors such as CD137, OX40, and GITR; and ligands such as CD137L (ligand for CD137), OX40L (ligand for OX40), and TNFSF18 (ligand for GITR).

In the present invention, the term "antagonist" includes various substances that interfere with receptor activation induced by binding between receptor and ligand. Examples of the antagonist include substances that interfere with the binding between receptor and ligand by binding to the receptor, and substances that interfere with the binding between receptor and ligand by binding to the ligand.

"An antagonist against an inhibitory immune checkpoint molecule" may be an antagonistic antibody that binds to an inhibitory immune checkpoint receptor (such as antagonistic anti-PD-1 antibody, anti-CTLA-4 antibody, anti-LAG-3 antibody, anti-TIM-3 antibody, anti-BTLA antibody, or the like); an antibody that binds to an inhibitory immune checkpoint ligand to inhibit its binding to the receptor (such as anti-PD-L1 antibody, anti-PD-L2 antibody, anti-CD80 antibody, anti-CD86 antibody, anti-GAL9 antibody, anti-HVEM antibody, or the like); a soluble polypeptide which is designed based on an inhibitory immune checkpoint ligand and does not activate the receptor, or a vector capable of expressing the polypeptide, or the like.

"An agonist against a co-stimulatory immune checkpoint molecule" may be an antibody having agonistic activity that binds to a co-stimulatory immune checkpoint receptor (such as agonistic anti-CD137 antibody, anti-OX40 antibody, anti-GITR antibody, or the like); a soluble polypeptide which is designed based on a co-stimulatory immune checkpoint ligand and has an action to activate the receptor, or a vector capable of expressing the polypeptide, or the like.

Methods for producing an antibody, and methods for producing a polypeptide by chemical synthesis or genetic engineering procedure are well-known conventional methods in the art. Those skilled in the art can prepare an antagonist against an inhibitory immune checkpoint molecule or an agonist against a co-stimulatory immune checkpoint molecule as described above by conventional methods. Methods for preparing a chimeric antibody, humanized antibody, or human antibody have also been established as well-known methods in the art. In cases where the anticancer drug targeting an immune checkpoint molecule is an antibody drug, an antigen-binding fragment such as Fab, $F(ab')_2$, or scFv (single chain fragment of variable region, single-chain antibody) may also be used, and methods for producing antigen-binding fragments are also well known.

Other preferred examples of the anticancer drugs that may be used in combination include anti-CD4 antibodies having cytotoxic activity; and anti-CD4 antibodies and antigen-binding fragments thereof which antibodies and fragments comprise a cytotoxic component bound thereto. The cytotoxic component herein means a substance having an activity to destroy living cells, and includes biological toxic substances, chemical substances, and radioactive substances. It is known that an anti-CD4 antibody having cytotoxic activity and an anti-CD4 antibody or antigen-binding fragment thereof which antibody or fragment comprises a cytotoxic component bound thereto have an antitumor effect on various cancers including blood cancers and solid cancers (for example, WO 2015/125652). The cytotoxic activity may be antibody-dependent cellular cytotoxicity (ADCC activity) or complement-dependent cellular cytotoxicity (CDC activity). It is necessary to use an antibody having high cytotoxic activity by which a sufficiently high ability to kill $CD4^+$ cells can be exerted.

The term "high cytotoxic activity" in the context of the ADCC activity means that an antibody has a higher ADCC activity than the known anti-CD4 antibody 6G5 or CE9.1 that is known to have an ADCC activity, when the ADCC activity against CD4-expressing cells is measured by a known measurement method. In the context of the CDC activity, the term means that an antibody has a stronger CDC activity than the known anti-CD4 antibody OKT4 that is known to have a CDC activity, when the CDC activity against CD4-expressing cells is measured in an experimental system using the same complements by a known measurement method.

Preferably, an anti-CD4 antibody having a high cytotoxic activity has an ADCC activity that is 10 times or more, more preferably 100 times or more higher than the ADCC activity of the known anti-CD4 antibody 6G5 and/or CE9.1, or has a CDC activity that is 10 times or more, more preferably 100 times or more higher than the CDC activity of the known anti-CD4 antibody OKT4. As used herein, the term "10 times or more" means, for example, that the minimum antibody concentration at which a given antibody exhibits a cytotoxic activity against a certain amount of cells is one-tenth or less of that of the above-described known antibody. As for the affinity of the anti-CD4 antibody to CD4, the antibody binding activity $K_D$ may be about $1 \times 10^{-9}$M or less.

Methods for measurement of the ADCC activity and the CDC activity of antibodies are known and described in e.g. Cancer Immunol. Immunother., 36, 373 (1993), and kits therefor are commercially available. Whether a given antibody has a higher cytotoxic activity than known anti-CD4 antibodies or not may be evaluated using such a commercially available kit. A specific example of measurement of the cytotoxic activity using a commercially available kit is described in the Examples below. The level of the ADCC activity of anti-CD4 antibody can also be evaluated by, as described in the Examples below, mixing human peripheral blood mononuclear cells with the anti-CD4 antibody, allowing the reaction to proceed at 37° C. for several hours, performing flow cytometry analysis to measure the ratio of CD3+ cells to CD8+ cells in the reaction solution, and then comparing the obtained measurement value with a measurement value obtained using an anti-CD4 antibody having no ADCC activity or a known anti-CD4 antibody described above.

An anti-CD4 antibody having a high cytotoxic activity can be prepared, for example, from a monoclonal anti-CD4 antibody prepared by a known method or from an already established known anti-CD4 antibody, by increasing the cytotoxicity of the antibody by a method known in the art. In cases where an anti-CD4 antibody that specifically recognizes CD4 expressed on the cell surface and has a strong cytotoxicity is known, such an antibody may be used as an effective ingredient of the agent of the present invention. For example, WO 2010/074266 discloses an anti-CD4 antibody having a higher ADCC activity than conventional anti-CD4 antibodies.

Methods for increasing the cytotoxic activity of an antibody are also known, and any of these methods may be used. Specific examples of known methods for enhancing the ADCC activity include the POTELLIGENT (registered trademark) technology, in which fucose (core fucose) contained in a sugar chain present in the Fc region of the antibody is removed (Yamane-Ohnuki N, Satoh M, Production of therapeutic antibodies with controlled fucosylation, MAbs 2009; 1: 230-236); a method in which fucose substrate donation is blocked; and a method in which a sugar chain present in the Fc region of the antibody is converted (M. Schuster et al., Improved effector functions of a therapeutic monoclonal Lewis Y-specific antibody by glycoform engineering, Cancer Res 2005; 65: 7934-7941). Examples of known methods for enhancing the CDC activity include the COMPLEGENT (registered trademark) technology, in which a part of the isotype IgG1 is combined with a sequence of the isotype IgG3 to increase the CDC activity (Natsume A, In M, Takamura H, et al. Engineered antibodies of IgG1/IgG3 mixed isotype with enhanced cytotoxic activities, Cancer Res. 2008; 68: 3863-3872). The AccretaMab (registered trademark) technology, in which the POTELLIGENT (registered trademark) technology and the COMPLEGENT (registered trademark) technology are employed in combination to increase both the ADCC activity and the CDC activity, thereby strongly increasing the cytotoxic activity of an antibody (Natsume A, et al., Improving effector functions of antibodies for cancer treatment: Enhancing ADCC and CDC, Drug Des Devel Ther. 2009; 3: 7-16) is also known.

The anticancer drugs that may be used in combination are not limited, and examples of the anticancer drug include: at least one selected from antagonistic antibodies against inhibitory immune checkpoint receptors and antigen-binding fragments thereof, antibodies against inhibitory immune checkpoint ligands and antigen-binding fragments thereof, agonistic antibodies against co-stimulatory immune checkpoint receptors and antigen-binding fragments thereof, anti-CD4 antibodies having cytotoxic activity, and anti-CD4 antibodies and antigen-binding fragments thereof which antibodies and fragments comprise a cytotoxic component bound thereto; at least one selected from antagonistic antibodies against inhibitory immune checkpoint receptors and antigen-binding fragments thereof, antibodies against inhibitory immune checkpoint ligands and antigen-binding fragments thereof, and anti-CD4 antibodies having cytotoxic activity; or at least one selected from antagonistic antibodies against inhibitory immune checkpoint receptors and antigen-binding fragments thereof, and anti-CD4 antibodies having cytotoxic activity. Especially preferred examples of the antagonistic antibodies against inhibitory immune checkpoint receptors include, but are not limited to, antagonistic anti-PD-1 antibodies and antagonistic anti-CTLA-4 antibodies, especially antagonistic anti-PD-1 antibodies.

In cases where the agent of the present invention is used in combination with a known anticancer drug or anti-inflammatory drug, the anticancer drug or anti-inflammatory drug may be used in the same manner as when it is used alone for treatment of cancer or treatment of an inflammatory disease. It is also possible to reduce the dose or dosage, the frequency of administration, the dosing period, etc. of drugs, since an increased effect is obtained thanks to combined use with the agent of the present invention.

Since a higher anticancer effect can be obtained by combined use of an anticancer drug and the agent of the present invention, the agent of the present invention can also be understood as having an effect to enhance the anticancer activity of an anticancer drug. When the agent of the present invention is used as an agent for enhancing anticancer activity of an anticancer drug, the subject to which the agent is administered is a cancer patient, i.e. a patient who is going to receive or receives treatment with the anticancer drug.

By identifying a derivative having a higher pharmacological effect than disulfiram from a library of derivatives having structures prepared by applying various chemical modifications to disulfiram, a compound having a still higher pharmacological effect as a FROUNT inhibitor or an agent for controlling microenvironment-constituting cells can be obtained. Aldehyde dehydrogenase-inhibiting activity of disulfiram is a side effect in application of disulfiram to a patient with a cancer or an inflammatory disease. Thus, reduction of the aldehyde dehydrogenase-inhibiting activity can also be used as an index for selection of an excellent derivative.

"Derivatives" are compounds obtained by introducing various chemical modifications into their original compound, and have structures similar to those of the original compound. In the process of optimization of lead compound in drug discovery, derivatives of the lead compound are sometimes called peripheral compounds. A library of such derivatives can be prepared by, for example, application of a method of combinatorial chemistry. Diethyldithiocarbamate is a compound having a structure generated from cleavage of the S—S bond of disulfiram, and the term "disulfiram derivative" in the present invention includes diethyldithiocarbamate derivatives. The disulfiram derivative may be, for example, a compound having the structure shown in the following Formula 1 or Formula 2, although the disulfiram derivative is not limited thereto.

Formula 1

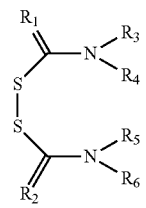

(wherein in Formula 1, $R_1$ and $R_2$ are each independently methyl that is optionally substituted by a sulfur atom(s), oxygen atom(s), and/or halogen atom(s); and $R_3$ to $R_6$ are each independently a hydrogen atom, $C_1$-$C_5$ linear alkyl, or $C_3$-$C_5$ branched alkyl, for example, $C_1$-$C_3$ linear alkyl or $C_3$ branched alkyl. The alkyl is optionally substituted by a halogen atom(s), and one or more carbon atoms constituting the alkyl is optionally replaced by a nitrogen atom(s), sulfur atom(s), and/or oxygen atom(s).)

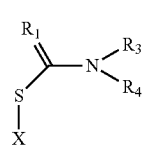

Formula 2

(wherein in Formula 2, $R_1$, $R_3$, and $R_4$ have the same meanings as in the Formula 1, and X is a hydrogen atom, halogen atom, alkali metal atom, or methyl that is optionally substituted by halogen atom.)

The method for identifying a disulfiram derivative having an improved ability to inhibit interaction between FROUNT protein and CCR2B or CCR5 may include, for example, the following steps.

(1) A FROUNT protein fragment, and a CCR2B fragment or a CCR5 fragment are incubated with a library of disulfiram derivatives.

As described later, the binding pocket structure through which FROUNT protein binds to CCR2B or CCR5 is constituted by a plurality of amino acid residues including at least one of the following seven residues: M564, T565, I568, A569, M575, L578, and L600. Accordingly, a region containing at least these seven residues, that is, a region containing the 564th to 600th amino acids, is used as the FROUNT protein fragment. It has been shown, by an HTRF experiment which was carried out in the past, that the fragment consisting of the region of the 549th to 656th amino acids and the fragment consisting of the region of the 532nd to 650th amino acids have an ability to bind to the C-terminal membrane-proximal region of CCR2 (data not shown). Thus, examples of the FROUNT protein fragment include a fragment containing the region of the 549th to the 650th amino acids, and a fragment containing the region of the 549th to 656th amino acids or the 532nd to 650th amino acids. Or, the FROUNT protein fragment may be a fragment containing the region of the 500th to the 656th amino acids.

The fragment consisting of the region of the 310th to the 325th amino acids of CCR2B (EKFRRYLSVFFRKHIT) is an especially preferred example of the CCR2B fragment used herein. However, even a fragment lacking a small number of terminal amino acid residues can have an ability to bind to FROUNT. Thus, a fragment containing the region of the 312th to 323rd amino acids, for example, a fragment containing the region of the 310th to 325th amino acids, of the CCR2B amino acid sequence shown in SEQ ID NO:6 can be used as the CCR2B fragment.

An especially preferred example of the CCR5 fragment is a fragment consisting of the region of the 302nd to 317th amino acids (EKFRNYLLVFFQKHIA). However, similarly to the above, even a fragment lacking a small number of terminal amino acid residues can have an ability to bind to FROUNT. Thus, a fragment containing the region of the 304th to 315th amino acids, for example, a fragment containing the region of the 302th to 317th amino acids, of the CCR5 amino acid sequence shown in SEQ ID NO:8 can be used as the CCR5 fragment.

The protein fragments described above can be prepared by a well-known chemical synthesis method or genetic engineering method.

(2) A disulfiram derivative having a higher activity to inhibit the binding between the FROUNT protein fragment and the CCR2B fragment or CCR5 fragment compared to disulfiram is selected. This step can be carried out using a well-known binding assay. The selected disulfiram derivative is useful as a disulfiram derivative having an improved ability to inhibit interaction between FROUNT protein and CCR2B or CCR5, and, in turn, as a disulfiram derivative having an improved ability to control microenvironment-constituting cells in lesions of cancers and inflammatory diseases.

(3) The disulfiram derivative may be further subjected to a step of measuring the aldehyde dehydrogenase-inhibiting activity to select a derivative having a lower level of the activity than that of the original disulfiram. This step is usually carried out after the step (2).

Candidate FROUNT inhibitor substances found by screening or the like other than disulfiram may also be subjected to synthesis/development of derivatives and a binding inhibition assay in the same manner as described above to identify a derivative compound having an improved FROUNT-inhibiting ability.

The derivative compound such as a disulfiram derivative identified as described above can be produced by a method well known in the field of chemical synthesis. The derivative has a better performance than disulfiram as an inhibitor of interaction between CCR2B or CCR5 and FROUNT protein, as an agent for controlling microenvironment-constituting cells such as an agent for controlling macrophage infiltration, and, in particular, as a pharmaceutical.

The present inventors have first clarified the spatial structure of the region in which FROUNT protein binds to CCR2B at the atomic coordinate level. By an NMR analysis of the state of binding between a fragment of the binding region of FROUNT protein and a fragment of the binding region of CCR2B, the following seven residues have been identified as candidates of residues constituting the binding pocket structure: methionine at position 564 (M564), threonine at position 565 (T565), isoleucine at position 568 (I568), alanine at position 569 (A569), methionine at position 575 (M575), leucine at position 578 (L578), and leucine at position 600 (L600). These seven residues are the top seven residues showing large chemical shift changes in the NMR signal due to formation of the complex, and the binding pocket through which FROUNT binds to CCR2B is constituted by a plurality of residues including at least one of these seven residues. The binding regions through which CCR2B and CCR5 bind to FROUNT, respectively, have almost the same spatial structure, and CCR5 also binds to the binding pocket structure identified herein. Since a variety of methods for drug design based on the spatial structure (SBDD: structure based drug design) and for in silico screening are known, more potent FROUNT inhibitors can be developed by utilizing the spatial structure information of FROUNT protein. Table 1 shows the atomic coordinate data of the seven residues described above, in the protein data bank format.

TABLE 1

| | | | | | | | | | | | |
|---|---|---|---|---|---|---|---|---|---|---|---|
| | Atomic coordinates of 7 residues defining a binding pocket | | | | | | | | | | |
| ATOM | 1 | N | MET | A | 564 | −12.289 | 7.512 | −6.831 | 1.00 | 75.12 | N |
| ATOM | 2 | CA | MET | A | 564 | −12.530 | 8.940 | −6.665 | 1.00 | 14.53 | C |
| ATOM | 3 | CB | MET | A | 564 | −13.865 | 9.335 | −7.280 | 1.00 | 35.23 | C |
| ATOM | 4 | CG | MET | A | 564 | −14.069 | 10.822 | −7.515 | 1.00 | 62.34 | C |
| ATOM | 5 | SD | MET | A | 564 | −15.851 | 11.125 | −7.713 | 1.00 | 64.33 | S |
| ATOM | 6 | CE | MET | A | 564 | −16.125 | 10.429 | −9.359 | 1.00 | 13.31 | O |
| ATOM | 7 | C | MET | A | 564 | −12.553 | 9.320 | −5.187 | 1.00 | 65.53 | C |
| ATOM | 8 | O | MET | A | 564 | −11.998 | 10.345 | −4.790 | 1.00 | 24.41 | O |
| ATOM | 9 | H | MET | A | 564 | −12.969 | 6.961 | −7.274 | 1.00 | 75.12 | H |
| ATOM | 10 | HA | MET | A | 564 | −11.724 | 9.471 | −7.148 | 1.00 | 14.53 | H |
| ATOM | 11 | HB2 | MET | A | 564 | −13.970 | 8.818 | −8.233 | 1.00 | 35.23 | H |
| ATOM | 12 | HB3 | MET | A | 564 | −14.657 | 8.989 | −6.612 | 1.00 | 35.23 | H |
| ATOM | 13 | HG2 | MET | A | 564 | −13.731 | 11.402 | −6.656 | 1.00 | 62.34 | H |
| ATOM | 14 | HG3 | MET | A | 564 | −13.529 | 11.186 | −8.391 | 1.00 | 62.34 | H |
| ATOM | 15 | HE1 | MET | A | 564 | −15.641 | 11.055 | −10.107 | 1.00 | 13.31 | H |
| ATOM | 16 | HE2 | MET | A | 564 | −15.752 | 9.415 | −9.440 | 1.00 | 13.31 | H |
| ATOM | 17 | HE3 | MET | A | 564 | −17.195 | 10.405 | −9.573 | 1.00 | 13.31 | H |
| ATOM | 18 | N | THR | A | 565 | −13.198 | 8.486 | −4.377 | 1.00 | 4.44 | N |
| ATOM | 19 | CA | THR | A | 565 | −13.293 | 8.735 | −2.944 | 1.00 | 12.13 | C |
| ATOM | 20 | CB | THR | A | 565 | −14.633 | 8.202 | −2.394 | 1.00 | 14.53 | C |
| ATOM | 21 | OG1 | THR | A | 565 | −14.866 | 6.864 | −2.852 | 1.00 | 13.12 | O |
| ATOM | 22 | CG2 | THR | A | 565 | −15.796 | 9.086 | −2.827 | 1.00 | 53.10 | C |
| ATOM | 23 | C | THR | A | 565 | −12.157 | 8.053 | −2.190 | 1.00 | 73.43 | C |
| ATOM | 24 | O | THR | A | 565 | −11.797 | 8.463 | −1.087 | 1.00 | 44.02 | O |
| ATOM | 25 | H | THR | A | 565 | −13.620 | 7.686 | −4.753 | 1.00 | 4.44 | H |
| ATOM | 26 | HA | THR | A | 565 | −13.228 | 9.802 | −2.785 | 1.00 | 12.13 | H |
| ATOM | 27 | HB | THR | A | 565 | −14.610 | 8.161 | −1.299 | 1.00 | 14.53 | H |
| ATOM | 28 | HG21 | THR | A | 565 | −15.786 | 10.036 | −2.286 | 1.00 | 53.10 | H |
| ATOM | 29 | HG22 | THR | A | 565 | −16.747 | 8.580 | −2.648 | 1.00 | 53.10 | H |
| ATOM | 30 | HG23 | THR | A | 565 | −15.756 | 9.308 | −3.898 | 1.00 | 53.10 | H |
| ATOM | 31 | HG1 | THR | A | 565 | −15.187 | 6.921 | −3.775 | 1.00 | 13.12 | H |
| ATOM | 32 | N | ILE | A | 568 | −6.488 | 6.792 | −3.580 | 1.00 | 2.13 | N |
| ATOM | 33 | CA | ILE | A | 568 | −5.657 | 6.386 | −4.706 | 1.00 | 71.23 | C |
| ATOM | 34 | CB | ILE | A | 568 | −6.073 | 4.952 | −5.170 | 1.00 | 74.31 | C |
| ATOM | 35 | CG2 | ILE | A | 568 | −5.149 | 3.922 | −4.498 | 1.00 | 22.21 | C |
| ATOM | 36 | CG1 | ILE | A | 568 | −7.542 | 4.597 | −4.880 | 1.00 | 32.44 | C |
| ATOM | 37 | CD1 | ILE | A | 568 | −8.044 | 3.281 | −5.459 | 1.00 | 42.43 | C |
| ATOM | 38 | C | ILE | A | 568 | −5.717 | 7.413 | −5.832 | 1.00 | 22.11 | C |
| ATOM | 39 | O | ILE | A | 568 | −4.695 | 7.761 | −6.423 | 1.00 | 72.44 | O |
| ATOM | 40 | H | ILE | A | 568 | −7.436 | 6.987 | −3.731 | 1.00 | 2.13 | H |
| ATOM | 41 | HA | ILE | A | 568 | −4.637 | 6.309 | −4.357 | 1.00 | 71.23 | H |
| ATOM | 42 | HB | ILE | A | 568 | −5.939 | 4.900 | −6.248 | 1.00 | 74.31 | H |
| ATOM | 43 | HG12 | ILE | A | 568 | −7.671 | 4.543 | −3.795 | 1.00 | 32.44 | H |
| ATOM | 44 | HG13 | ILE | A | 568 | −8.187 | 5.396 | −5.258 | 1.00 | 32.44 | H |
| ATOM | 45 | HG21 | ILE | A | 568 | −4.096 | 4.163 | −4.675 | 1.00 | 22.21 | H |
| ATOM | 46 | HG22 | ILE | A | 568 | −5.309 | 3.895 | −3.415 | 1.00 | 22.21 | H |
| ATOM | 47 | HG23 | ILE | A | 568 | −5.318 | 2.916 | −4.888 | 1.00 | 22.21 | H |
| ATOM | 48 | HD11 | ILE | A | 568 | −9.056 | 3.073 | −5.097 | 1.00 | 42.43 | H |
| ATOM | 49 | HD12 | ILE | A | 568 | −8.102 | 3.334 | −6.547 | 1.00 | 42.43 | H |
| ATOM | 50 | HD13 | ILE | A | 568 | −7.420 | 2.430 | −5.176 | 1.00 | 42.43 | H |
| ATOM | 51 | N | ALA | A | 569 | −6.920 | 7.896 | −6.121 | 1.00 | 55.14 | N |
| ATOM | 52 | CA | ALA | A | 569 | −7.113 | 8.887 | −7.173 | 1.00 | 73.42 | C |
| ATOM | 53 | CB | ALA | A | 569 | −8.485 | 8.814 | −7.805 | 1.00 | 24.43 | C |
| ATOM | 54 | C | ALA | A | 569 | −6.857 | 10.297 | −6.653 | 1.00 | 32.11 | C |
| ATOM | 55 | O | ALA | A | 569 | −7.599 | 10.823 | −5.823 | 1.00 | 73.40 | O |
| ATOM | 56 | H | ALA | A | 569 | −7.697 | 7.580 | −5.614 | 1.00 | 55.14 | H |
| ATOM | 57 | HA | ALA | A | 569 | −6.411 | 8.673 | −7.966 | 1.00 | 73.42 | H |
| ATOM | 58 | HB1 | ALA | A | 569 | −8.533 | 9.430 | −8.705 | 1.00 | 24.43 | H |
| ATOM | 59 | HB2 | ALA | A | 569 | −8.718 | 7.788 | −8.081 | 1.00 | 24.43 | H |
| ATOM | 60 | HB3 | ALA | A | 569 | −9.260 | 9.175 | −7.135 | 1.00 | 24.43 | H |
| ATOM | 61 | N | MET | A | 575 | −11.112 | 15.090 | −11.894 | 1.00 | 25.14 | N |
| ATOM | 62 | CA | MET | A | 575 | −11.628 | 15.906 | −12.986 | 1.00 | 51.31 | C |
| ATOM | 63 | CB | MET | A | 575 | −10.501 | 16.866 | −13.456 | 1.00 | 0.12 | C |
| ATOM | 64 | CG | MET | A | 575 | −10.911 | 18.314 | −13.742 | 1.00 | 24.30 | C |
| ATOM | 65 | SD | MET | A | 575 | −11.759 | 18.561 | −15.335 | 1.00 | 20.34 | S |
| ATOM | 66 | CE | MET | A | 575 | −13.473 | 18.648 | −14.761 | 1.00 | 11.54 | C |
| ATOM | 67 | C | MET | A | 575 | −12.075 | 15.032 | −14.154 | 1.00 | 1.33 | C |
| ATOM | 68 | O | MET | A | 575 | −13.076 | 15.319 | −14.810 | 1.00 | 54.34 | O |
| ATOM | 69 | H | MET | A | 575 | −10.232 | 15.299 | −11.516 | 1.00 | 25.14 | H |
| ATOM | 70 | HA | MET | A | 575 | −12.481 | 16.455 | −12.615 | 1.00 | 51.31 | H |
| ATOM | 71 | HB2 | MET | A | 575 | −9.742 | 16.938 | −12.665 | 1.00 | 0.12 | H |
| ATOM | 72 | HB3 | MET | A | 575 | −9.970 | 16.453 | −14.324 | 1.00 | 0.12 | H |
| ATOM | 73 | HG2 | MET | A | 575 | −11.496 | 18.734 | −12.919 | 1.00 | 24.30 | H |
| ATOM | 74 | HG3 | MET | A | 575 | −9.996 | 18.915 | −13.802 | 1.00 | 24.30 | H |
| ATOM | 75 | HE1 | MET | A | 575 | −13.756 | 17.753 | −14.206 | 1.00 | 11.54 | H |
| ATOM | 76 | HE2 | MET | A | 575 | −13.610 | 19.529 | −14.130 | 1.00 | 11.54 | H |
| ATOM | 77 | HE3 | MET | A | 575 | −14.136 | 18.739 | −15.625 | 1.00 | 11.54 | H |
| ATOM | 78 | N | LEU | A | 578 | −15.411 | 12.762 | −12.695 | 1.00 | 23.52 | N |

TABLE 1-continued

Atomic coordinates of 7 residues defining a binding pocket

| ATOM | 79 | CA | LEU | A | 578 | −16.674 | 13.490 | −12.667 | 1.00 | 14.05 | C |
| --- | --- | --- | --- | --- | --- | --- | --- | --- | --- | --- | --- |
| ATOM | 80 | CB | LEU | A | 578 | −16.406 | 14.884 | −12.091 | 1.00 | 22.03 | C |
| ATOM | 81 | CG | LEU | A | 578 | −16.883 | 15.021 | −10.649 | 1.00 | 24.35 | C |
| ATOM | 82 | CD1 | LEU | A | 578 | −18.399 | 15.040 | −10.615 | 1.00 | 73.11 | C |
| ATOM | 83 | CD2 | LEU | A | 578 | −16.278 | 13.975 | −9.733 | 1.00 | 23.41 | C |
| ATOM | 84 | C | LEU | A | 578 | −17.241 | 13.653 | −14.073 | 1.00 | 63.24 | C |
| ATOM | 85 | O | LEU | A | 578 | −18.444 | 13.507 | −14.291 | 1.00 | 51.34 | O |
| ATOM | 86 | H | LEU | A | 578 | −14.633 | 13.138 | −12.234 | 1.00 | 23.52 | H |
| ATOM | 87 | HA | LEU | A | 578 | −17.373 | 12.918 | −12.074 | 1.00 | 14.05 | H |
| ATOM | 88 | HB2 | LEU | A | 578 | −15.339 | 15.138 | −12.137 | 1.00 | 22.03 | H |
| ATOM | 89 | HB3 | LEU | A | 578 | −16.901 | 15.648 | −12.695 | 1.00 | 22.03 | H |
| ATOM | 90 | HG | LEU | A | 578 | −16.561 | 15.982 | −10.266 | 1.00 | 24.35 | H |
| ATOM | 91 | HD11 | LEU | A | 578 | −18.829 | 14.046 | −10.754 | 1.00 | 73.11 | H |
| ATOM | 92 | HD12 | LEU | A | 578 | −18.799 | 15.682 | −11.405 | 1.00 | 73.11 | H |
| ATOM | 93 | HD13 | LEU | A | 578 | −18.727 | 15.452 | −9.661 | 1.00 | 73.11 | H |
| ATOM | 94 | HD21 | LEU | A | 578 | −16.750 | 13.008 | −9.897 | 1.00 | 23.41 | H |
| ATOM | 95 | HD22 | LEU | A | 578 | −16.423 | 14.239 | −8.687 | 1.00 | 23.41 | H |
| ATOM | 96 | HD23 | LEU | A | 578 | −15.199 | 13.879 | −9.893 | 1.00 | 23.41 | H |
| ATOM | 97 | N | LEU | A | 600 | −19.544 | 13.013 | −5.696 | 1.00 | 1.43 | N |
| ATOM | 98 | CA | LEU | A | 600 | −18.998 | 13.511 | −6.954 | 1.00 | 22.52 | C |
| ATOM | 99 | CB | LEU | A | 600 | −20.004 | 13.245 | −8.081 | 1.00 | 34.01 | C |
| ATOM | 100 | CG | LEU | A | 600 | −19.798 | 11.901 | −8.793 | 1.00 | 34.23 | C |
| ATOM | 101 | CD1 | LEU | A | 600 | −19.738 | 10.710 | −7.845 | 1.00 | 64.24 | C |
| ATOM | 102 | CD2 | LEU | A | 600 | −20.943 | 11.693 | −9.769 | 1.00 | 74.25 | C |
| ATOM | 103 | C | LEU | A | 600 | −18.631 | 14.987 | −6.843 | 1.00 | 23.25 | C |
| ATOM | 104 | O | LEU | A | 600 | −17.455 | 15.348 | −6.878 | 1.00 | 1.43 | O |
| ATOM | 105 | H | LEU | A | 600 | −20.400 | 12.537 | −5.703 | 1.00 | 1.43 | H |
| ATOM | 106 | HA | LEU | A | 600 | −18.104 | 12.945 | −7.173 | 1.00 | 22.52 | H |
| ATOM | 107 | HB2 | LEU | A | 600 | −21.030 | 13.293 | −7.713 | 1.00 | 34.01 | H |
| ATOM | 108 | HB3 | LEU | A | 600 | −19.960 | 14.035 | −8.828 | 1.00 | 34.01 | H |
| ATOM | 109 | HG | LEU | A | 600 | −18.863 | 11.943 | −9.360 | 1.00 | 34.23 | H |
| ATOM | 110 | HD11 | LEU | A | 600 | −18.919 | 10.800 | −7.130 | 1.00 | 64.24 | H |
| ATOM | 111 | HD12 | LEU | A | 600 | −19.562 | 9.787 | −8.403 | 1.00 | 64.24 | H |
| ATOM | 112 | HD13 | LEU | A | 600 | −20.673 | 10.596 | −7.289 | 1.00 | 64.24 | H |
| ATOM | 113 | HD21 | LEU | A | 600 | −20.873 | 10.725 | −10.254 | 1.00 | 74.25 | H |
| ATOM | 114 | HD22 | LEU | A | 600 | −20.958 | 12.466 | −10.541 | 1.00 | 74.25 | H |
| ATOM | 115 | HD23 | LEU | A | 600 | −21.888 | 11.707 | −9.227 | 1.00 | 74.25 | H |

For example, by constructing a binding pocket structure through which FROUNT protein binds to CCR2B in silico using at least part of the identified atomic coordinates of FROUNT protein, calculating the strength of binding of the binding pocket structure to a compound library, and then selecting a compound that forms a stable complex with FROUNT protein, a novel substance that inhibits interaction between FROUNT protein and CCR2B or CCR5 can be identified. Databases in which the structure information of a number of compounds is registered are known, and such databases can be utilized as a compound library mentioned herein. By performing binding simulation on a library, evaluating the strength of the bindings based on the binding energy (chemical interaction energy), and selecting a compound, a compound expected to be capable of strongly binding to the binding pocket structure through which FROUNT protein binds to CCR2B (that is, capable of inhibiting binding between FROUNT protein and CCR2B or CCR5) can be selected.

By binding a candidate compound in silico to a binding pocket structure through which FROUNT protein binds to CCR2B, which structure is constructed based on the atomic coordinates, and evaluating the strength of the binding by calculation of the binding energy or the like, molecular designing of a candidate compound can be advanced such that a more stable complex can be formed. The structures of disulfiram and other candidate compounds can be modified into more desirable structures.

EXAMPLES

The present invention is described below by way of Examples more concretely. However, the present invention is not limited to the Examples described below. All the animal experiments were carried out in accordance with the guidelines of the Animal Care and Use Committee of the University of Tokyo.

1. Disulfiram Inhibits FROUNT-CCR2 Interaction

[Methods]

High-Throughput Screening Based on HTRF (Homogeneous Time Resolved Fluorescence) Method For the screening, a compound library containing 131,200 kinds of compounds dissolved in DMSO at a concentration of 10 mM or 2 mM (obtained from Open Innovation Center for Drug Discovery, the University of Tokyo) was used. The HTRF assay was carried out using a 384-well low-dose white microplate (Corning Coaster; catalog number 3676). In each well, 4 μL of a solution of 20 nM GST fusion FROUNT protein (a recombinant polypeptide prepared by fusing GST to aa 500-656 of SEQ ID NO:2), and DMSO or test compounds were mixed with a binding buffer (10 mM HEPES [pH 7.4], 0.2 M potassium fluoride, 10 mM NaCl, 0.1% Tween 20, and 0.5% bovine serum albumin [BSA]), and the plate was incubated at room temperature for 30 minutes. After the incubation, biotinylated CCR2 pro-C peptide (prepared by biotinylation of the 16 residues EKFRRYLSVFFRKHIT in the C-terminal region of CCR2B (SEQ ID NO:3)) at a final concentration of 250 nM, 2.6 ng of a europium cryptate-labelled anti-GST antibody, and 12.5 ng of high-grade XL665-conjugated streptavidin were added to each well. After incubation at room temperature for 20 hours, the HTRF signal was measured at emission wavelengths of 620 nm and 665 nm using a multilabel counter EnVision (PerkinElmer).

Binding Inhibition Assay Based on HTRF Method

By the same HTRF assay as described above, the abilities of disulfiram to inhibit the FROUNT-CCR2 interaction or the FROUNT-CCR5 interaction were investigated. As the CCR5 pro-C peptide, the 16 residues EKFRNYLL-VFFQKHIA (SEQ ID NO:4) in the C-terminal region of CCR5 was used. As a control, the p53-MDM2 interaction (which is inhibited by an MDM-2-specific inhibitor Nutlin), which is also a helix peptide-protein interaction like the interaction between FROUNT and CCR2 or CCR5 but is not related thereto, was used.

[Results]

Disulfiram selectively inhibited the interactions between FROUNT-CCR2 and between FROUNT-CCR5, but did not inhibit the interaction between p53-MDM2 (FIG. 1a). The IC50 of disulfiram against FROUNT-CCR2 was calculated as 42 nM, which indicates about 100 times higher inhibitory action than that against p53-MDM2 (FIG. 1b).

The S—S bond of disulfiram (DSF) is decomposed by glutathione reductase in the body to generate diethyldithiocarbamate (DDC), and DDC is further metabolized to generate Me-DTC sulfoxide and Me-DTC sulfone. The result of investigation of the abilities of these metabolites to inhibit FROUNT is shown in Table 2. We investigated the FROUNT-inhibiting ability using sodium diethyldithiocarbamate as DDC to find that IC50 was 137 nM. Me-DTCs had an aldehyde dehydrogenase (ALDH)-inhibiting activity, but did not inhibit FROUNT. Thus, it was confirmed that the active substances responsible for inhibition of FROUNT and inhibition of ALDH are different from each other.

bond of disulfiram was not decomposed (by modification of S—S into S—$CH_2$—$CH_2$—S or S—$CH_2$—S), the ability to inhibit the interaction between FROUNT-CCR2 was lost.

[Reference]

Toda, E. et al. Identification of a binding element for the cytoplasmic regulator FROUNT in the membrane-proximal C-terminal region of chemokine receptors CCR2 and CCR5. Biochem J 457, 313-322, doi:10.1042/BJ20130827 (2014).

2. Disulfiram Directly Binds to FROUNT

[Methods]

Surface Plasmon Resonance Method

Interactions between FROUNT and compounds in the library were analyzed by surface plasmon resonance (SPR) using Biacore TI00 (GE Healthcare). Full-length FROUNT protein (SEQ ID NO:2) (Esaki, K. et al. Protein Expr Purif 77, 86-91, (2011)) was immobilized on a CM5 sensor chip. Solutions of disulfiram prepared by serial dilution in HBS-EP buffer containing 2% DMSO (GE Healthcare) were applied to the sensor chip at a flow rate of 30 μL/min. The resonance unit (RU) was measured during the process from the binding to the washing to analyze the binding dynamics. Biacore T100 evaluation software was used to carry out solvent correction for DMSO.

NMR Analysis of Spatial Structure of FROUNT Binding Region Complex

A fragment consisting of the region of the 500th to 656th amino acids of FROUNT protein and a CCR2 pro-C region

TABLE 2

| Compound | Structure | ALDH inhibition | FROUNT inhibition | p53 inhibition |
|---|---|---|---|---|
| DSF | (disulfiram structure) | 7400 nM* | 42 nM | >1000 nM |
| DDC | (sodium diethyldithiocarbamate structure) | n.d. | 137 nM | >1000 nM |
| Me-DTC sulfoxide | (Me-DTC sulfoxide structure) | 930 nM* | >1000 nM | >1000 nM |
| Me-DTC sulfone | (Me-DTC sulfone structure) | 530 nM* | >1000 nM | >1000 nM |

*Excerpt from Alcohol Clin Exp Res 1996.20.595-

We also investigated the FROUNT-inhibiting abilities of the zinc complex and the iron (III) complex of DDC to find that the IC50 values were 114.6 nM and 9.2 nM, respectively. In compounds that were modified such that the S—S fragment of 16 residues (SEQ ID NO:3) were prepared, and the binding state between the two fragments and the binding state between FROUNT protein and disulfiram were investigated by NMR analysis.

[Results]

Figure 2:
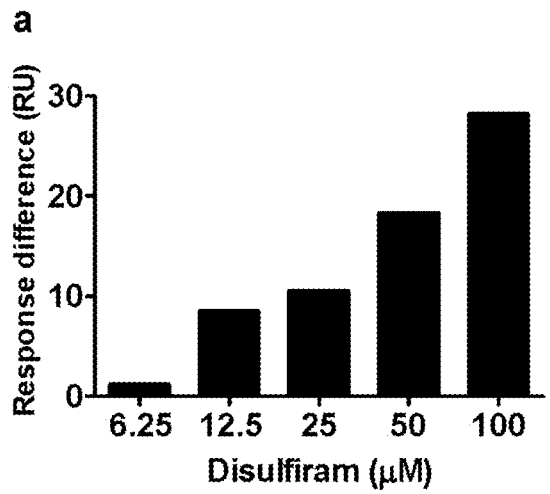
FIG. 2(a) shows the result of investigation of binding of disulfiram to FROUNT by SPR.
FIG. 2(b) shows a spatial structure model of the complex between disulfiram and the disulfiram-binding region on a FROUNT C-terminal fragment identified by NMR analysis. The FROUNT C-terminal fragment is shown as a ribbon model, and disulfiram is shown as a hard-sphere model diagram.
Figure 2:
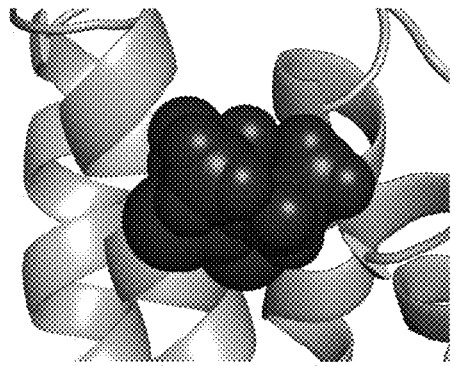

The SPR experiment revealed that disulfiram did not bind to CCR2 but directly bound to FROUNT protein (FIG. 2a). In the NMR analysis, the signal derived from FROUNT was affected by addition of disulfiram, suggesting that FROUNT and disulfiram directly interact with each other (FIG. 2b). It was also suggested that dimethyldithiocarbamate, a metabolite of disulfiram, binds to the same binding site on FROUNT as disulfiram (data not shown).

The analysis by chemical shift perturbation using NMR revealed that the residues M564, T565, I568, A569, M575, L578, and L600 showed large chemical shifts in the NMR signal due to formation of the FROUNT-CCR2 complex. The binding pocket through which CCR2 binds to FROUNT protein is thought to be constituted by a plurality of residues including at least one of these seven residues. The atomic coordinates of these seven residues are as shown in the Table 1 described above.

3. Disulfiram Inhibits Tumor Hyperplasia

[Methods]

Tumor Model

For evaluation of the subcutaneous tumor growth, LLC (Lewis lung cancer) cells ($5\times10^5$) were suspended in 50 µL of PBS, and subcutaneously administered to the right abdomen of each mouse. The tumor size was measured using a caliper twice a week. The tumor volume was calculated according to the following equation.

$$\text{Tumor volume} = (\text{tumor shorter diameter})^2 \times \text{tumor longer diameter}/2$$

In order to investigate the antitumor effect in the subcutaneous tumor growth model, disulfiram was added in an amount of 0.8 mg/g to CE-2 powder feed (CLEA Japan, Inc.) supplemented with 5% sucrose (Wako), and the mice were fed therewith every day during the period from Day 4 to Day 11 post tumor inoculation. The control group was fed with a feed supplemented with the same amount of sucrose.

[Results]

Figure 3:
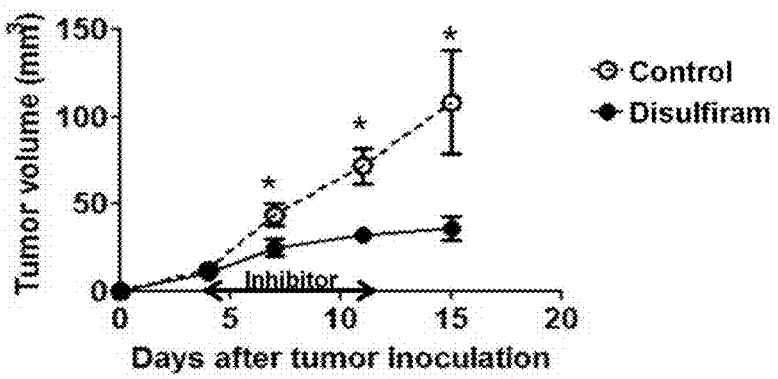
FIG. 3 shows the result of measurement of the tumor size in mice orally fed with a disulfiram-containing food or a control food. * indicates a significant difference at $p<0.05$.

In the mouse group to which disulfiram was orally given, the tumor volume was significantly smaller than that in the control group (FIG. 3). It was revealed that, by inhibiting FROUNT with disulfiram, the proliferation of lung cancer cells transplanted into the body can be inhibited.

4. Disulfiram Inhibits Formation of Tumor Metastatic Lesions

[Methods]

To provide a lung metastasis model, $1\times10^6$ B16F10 melanoma cells were suspended in 200 µL of PBS, and administered from the tail vein of each of wild-type C57BL/6 mice. Administration of the inhibitor was carried out one day before, 30 minutes before, and one day after the tumor administration. To provide a control, DMSO and a pyrimidine fluoride anticancer drug 5-FU were administered. The mice were euthanized on Day 9 post tumor administration, and PBS was perfused from the left ventricle, followed by isolation of lungs. Visible lung metastatic lesions in the left lobe were counted.

[Results]

Figure 4:
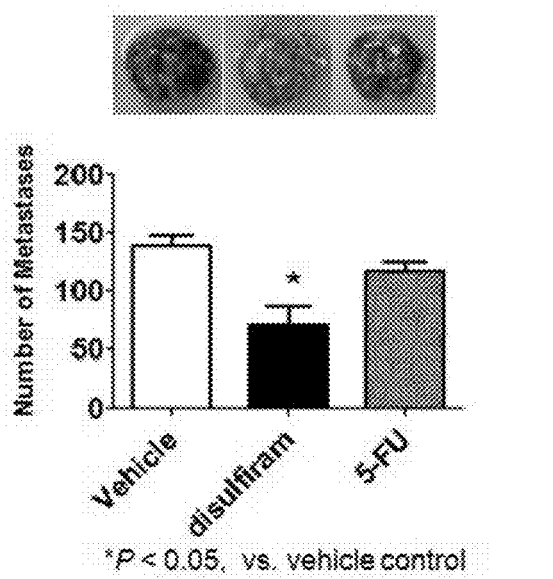
FIG. 4 shows photographs of metastatic nodules in lungs on Day 9 post tumor administration, and a graph showing the result of counting of metastasis.

FIG. 4 shows photographs of metastatic nodules on Day 9 post tumor administration, and a graph showing the result of counting of metastatic lesions. Disulfiram significantly reduced formation of lung metastatic lesions caused by the transplanted B16F10 cells.

5. Disulfiram Inhibits Tumor not Depending on Direct Cytocidal Action

[Methods]

Cytotoxicity and Proliferation Assays

The cytotoxicity of inhibitors was tested by using LDH Cytotoxicity Detection Kit (TaKaRa) according to the manufacturer's instructions. Briefly, tumor cells were cultured in the presence or absence of an agent (disulfiram or 5FU) for 72 hours, and the culture supernatant was then collected and tested for the concentration of lactate dehydrogenase released from damaged cells. For measurement of cell proliferation, cells were incubated in a plate well together with an inhibitor for 48 hours. During the last 30 minutes, WST-1 (Dojindo Laboratories) was added to the culture liquid, and the absorbance of each well was measured at 450 nm versus 650 nm reference using EnVision (PerkinElmer) to detect the formazan level.

[Results]

Figure 5:
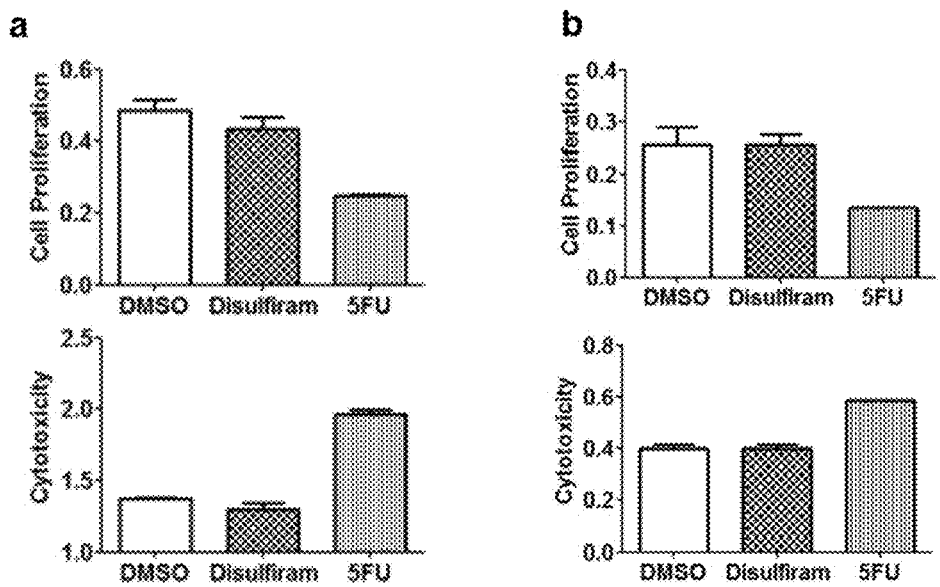
FIG. 5 shows the result of investigation of the growth-inhibiting actions and the cytotoxic activities of disulfiram and 5FU. a, LLC tumor cells; b, B16F10 melanoma cells.

Recently, it has been reported that disulfiram has an activity to directly kill certain types of tumor cells (Chen, D., et al., Cancer Res 66, 10425-10433, (2006); and Chiba, T. et al., PLoS One 9, e84807, (2014)). To investigate whether the antitumor activity of disulfiram is mediated by direct killing of tumor cells, we compared disulfiram with a cytotoxic anticancer drug 5FU for their anticancer actions and cytotoxic activities. As a result, disulfiram did not show cytotoxic activity at a concentration at which 5FU completely killed LLC tumor cells (FIG. 5a). 5FU also showed cytotoxic activity and growth-inhibiting action on B16F10 melanoma cells, but disulfiram did not show any action on the tumor cells at the same concentration (FIG. 5b). As shown in FIG. 4, 5FU did not reduce metastasis of B16F10 tumor despite its tumor-killing activity, whereas, disulfiram effectively reduced metastasis of the tumor at the same dose. These results indicate that the antitumor effect of disulfiram on B16F10 melanoma cells and LLC cells is not due to the cytotoxic activity, but due to its action on the tumor microenvironment in the host.

6. FROUNT is Highly Expressed in Macrophages

[Methods]

Preparation of FROUNT-Gfp-Knock-in Mice

By a conventional method, FROUNT-gfp knock-in mice were prepared by incorporating a GFP gene downstream of the FROUNT promoter on the mouse genome.

Flow Cytometry

Mice were intraperitonealy injected with 2 mL of 4% thioglycolate to induce peritonitis, and infiltrating cells in the peritoneum were collected from these mice. The cells were washed with PBS supplemented with 2% fetal bovine serum, resuspended, and then filtered through a 70-µm strainer. The Fc receptor was blocked by incubation with an anti-mouse CD16/32 antibody (BD biosciences), and thereafter the cells were stained with a fluorescently labeled antibody. Anti-mouse CD11b-Pacific Blue, anti-mouse Ly6C-APC-Cy7, anti-mouse Ly6G-Alexa Fluor 700, anti-mouse CD4-FITC, and anti-mouse B220-PE-Cy7 were purchased from Biolegend. Anti-mouse CD8-Pacific Blue was purchased from BD biosciences.

[Results]

Figure 6:
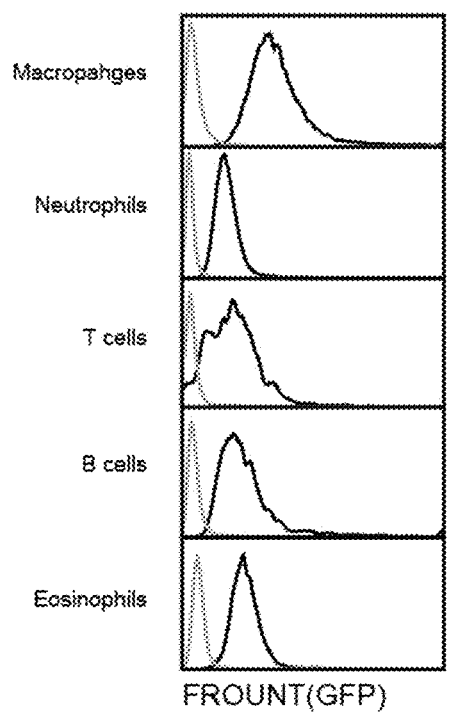
FIG. 6 shows the expression level of FROUNT in each type of cells collected from peritoneal inflammatory sites in wild-type mice and FROUNT-GFP knock-in mice. The expression level in each type of the cells was detected by flow cytometry analysis using antibodies against surface markers of various immune cells. Gray curves correspond to cells derived from the wild-type mice, and black curves correspond to cells derived from the GFP knock-in mice.

Flow cytometry analysis of cells derived from the FROUNT-GFP knock-in mice revealed that FROUNT was highly expressed especially in macrophases among the immune cells recruited into the inflammatory sites in the peritonitis model (FIG. 6). It was shown that monocytes/macrophages highly expressing FROUNT were enriched in the cell population mobilized by CCL2, and that FROUNT was highly expressed in cells expressing its receptor CCR2 (data not shown).

In view of the fact that FROUNT is highly expressed in monocytes/macrophages, and the fact that FROUNT has an ability to bind to CCR2 and CCR5 expressed on monocytes/macrophages (Toda, E. et al. J Immunol 183, 6387-6394, (2009)), we subsequently investigated whether deficiency of FROUNT influences infiltration of macrophages into inflammatory sites and tumor sites.

7. Hyperplasia and Metastasis of Cancer are Reduced in FROUNT-Deficient Mice

To investigate the role of FROUNT in a tumor microenvironment, mice in which FROUNT was knocked out were prepared using the cre/loxP system. Since complete deficiency of FROUNT causes embryonic lethality, conditional knockout was carried out using a system in which induction of recombination reaction was mediated by tamoxifen.

A targeting vector in which the genomic region containing exons 15 to 19 of the FROUNT gene was sandwiched between LoxP sequences was introduced into mice, and heterozygous $FNT^{flox}$ mice were crossed to create homozygous $FNT^{flox/flox}$ mice. Subsequently, B6.Cg-Tg(CAG-cre/Esr1*)5Amc/J mice (Jaxon Laboratory), to which Cre-ER, a fusion protein of Cre recombinase and a mutant estrogen receptor, was introduced, were crossed with the $FNT^{flox/flox}$ mice to obtain tamoxifen-inducible FROUNT conditional knockout mice FNT-cKO. By treating the FNT-cKO mice with tamoxifen, deletion of FROUNT was induced in both the genomic DNA and mRNA. It was confirmed that the expression of FROUNT mRNA was suppressed to half or less in the FNT-cKO mice treated with tamoxifen.

From 6 days or 14 days before the experiment, 8- to 16-week-old $FNT^{flox/flox}$ mice and FNT-cKO mice were fed with CE-2 powder feed (CLEA Japan, Inc.) supplemented with tamoxifen citrate (Wako Pure Chemical Industries, Ltd.) in an amount of 0.4 mg/1 g CE-2, to induce expression of Cre. Southern blotting was carried out to confirm the recombination.

(1) Reduction of Cancer Hyperplasia in FNT-cKO Mice

Figure 7:
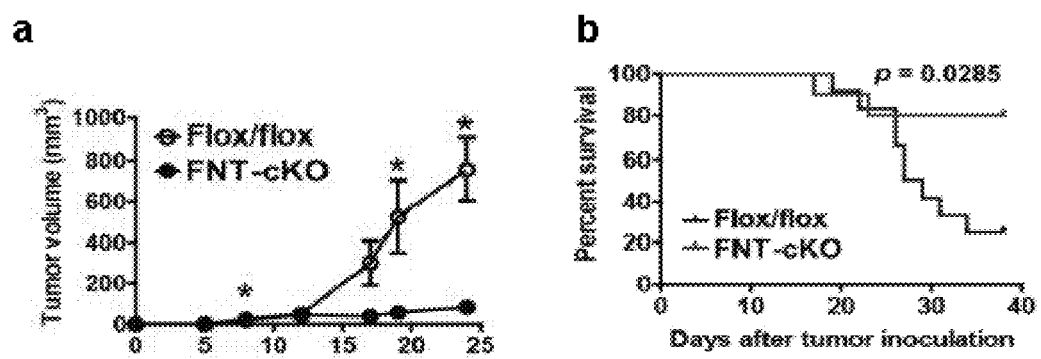
FIG. 7 shows the tumor volume (a) in and the survival rate (b) of FROUNT-deficient mice (FNT-cKO) in which FROUNT was conditionally knocked out and non-deficient mice (Flox/flox) transplanted with melanoma cells.

To the right abdomen of each of $FNT^{flox/flox}$ mice and FNT-cKO mice, $5\times10^5$ B16 melanoma cells were transplanted. Thereafter, the tumor size was measured using a caliper twice a week, and the tumor volume was calculated. As a result, significant tumor growth inhibition and improved survival rate were observed in FNT-cKO mice compared to non-knockout ($FNT^{flox/flox}$) mice (FIGS. 7a and 7b).

(2) Reduction of Cancer Metastasis in FNT-cKO Mice

Figure 8:
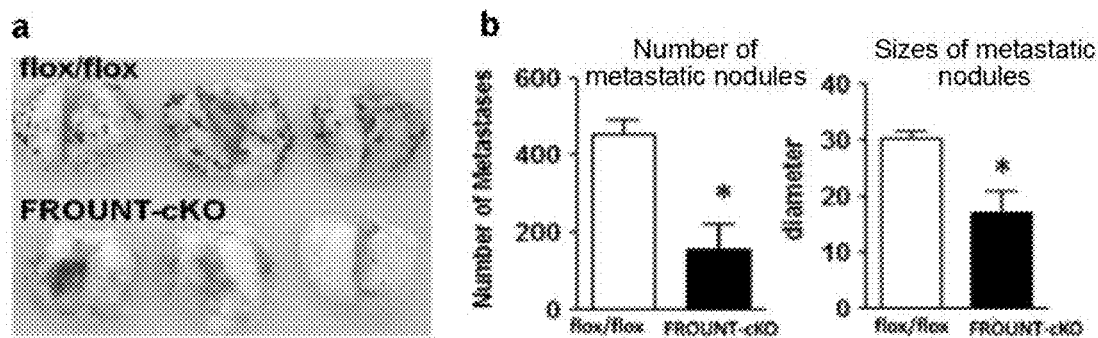
FIG. 8 shows the number and the size of metastatic nodules in lungs in a lung metastasis model of FROUNT-deficient mice (FROUNT-cKO) and non-deficient mice (Flox/flox).

To each of $FNT^{flox/flox}$ mice and FNT-cKO mice, $1\times10^6$ B16 melanoma cells were intravenously administered, and the numbers and the sizes of metastatic nodules in lungs were visually observed on Day 8 post administration. As a result, it was revealed that both the numbers and the sizes of metastatic nodules were significantly decreased in FNT-cKO mice (FIGS. 8a and 8b).

8. Macrophage Infiltration into Inflammatory Sites is Inhibited in FROUNT-Deficient Mice

[Methods]

In Vivo Chemotaxis Assay

Peritonitis was induced by intraperitoneal administration of 2 mL of 4% thioglycolate medium (Difco) to each of $FNT^{flox/flox}$ mice and FNT-cKO mice. Infiltrating cells in the peritoneum were collected by injecting 5 mL of ice-cold PBS into the abdominal cavity and giving a gentle massage. The collected cells was washed with PBS containing 0.1% FBS, and then subjected to flow cytometry analysis to investigate the cell number and the cell populations.

[Results]

Figure 9:
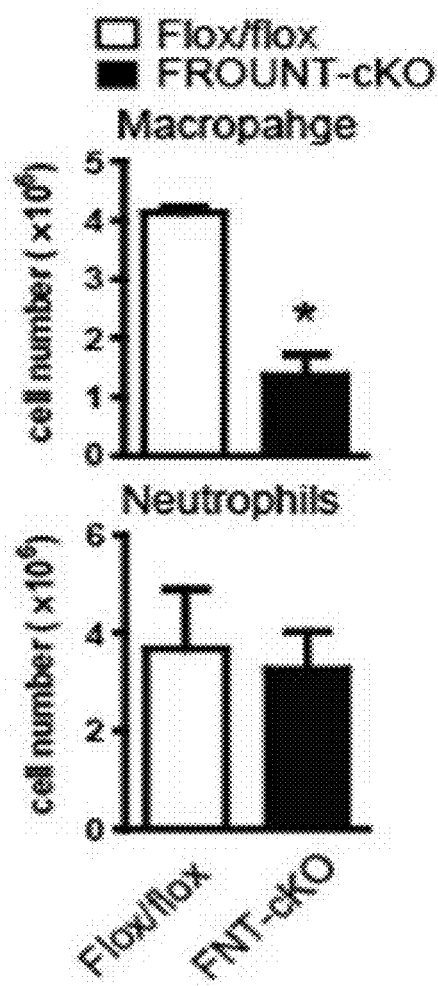
FIG. 9 shows the number of macrophages (upper panel) and the number of neutrophils (lower panel) in cell populations collected from peritoneal inflammatory sites in FROUNT-deficient mice (FROUNT-cKO) and non-deficient mice (Flox/flox).

The results are shown in FIG. 9. The number of macrophages was decreased in FROUNT-deficient mice, confirming that infiltration of macrophages into peritoneal inflammatory sites was reduced in these mice (FIG. 9, upper panel). No difference was found in the number of neutrophils between the FROUNT-deficient mice and the non-deficient mice (FIG. 9, lower panel).

9. Disulfiram Inhibits Infiltration of Macrophages into Inflammatory Sites

[Methods]

In Vivo Chemotaxis Assay

The same treatment as in the above-described section 8 was carried out on wild-type mice to induce peritonitis, and infiltrating cells in the peritoneum were collected. After washing the collected cells, flow cytometry analysis was carried out to investigate the cell number and the cell populations. For evaluation of disulfiram, disulfiram was dissolved in DMSO, and then diluted in 2% Tween 80-containing physiological saline to each concentration shown in the figure. Each resulting disulfiram solution was administered to mice 1 day before and 30 minutes before the administration of thioglycolate.

[Results]

Figure 10:
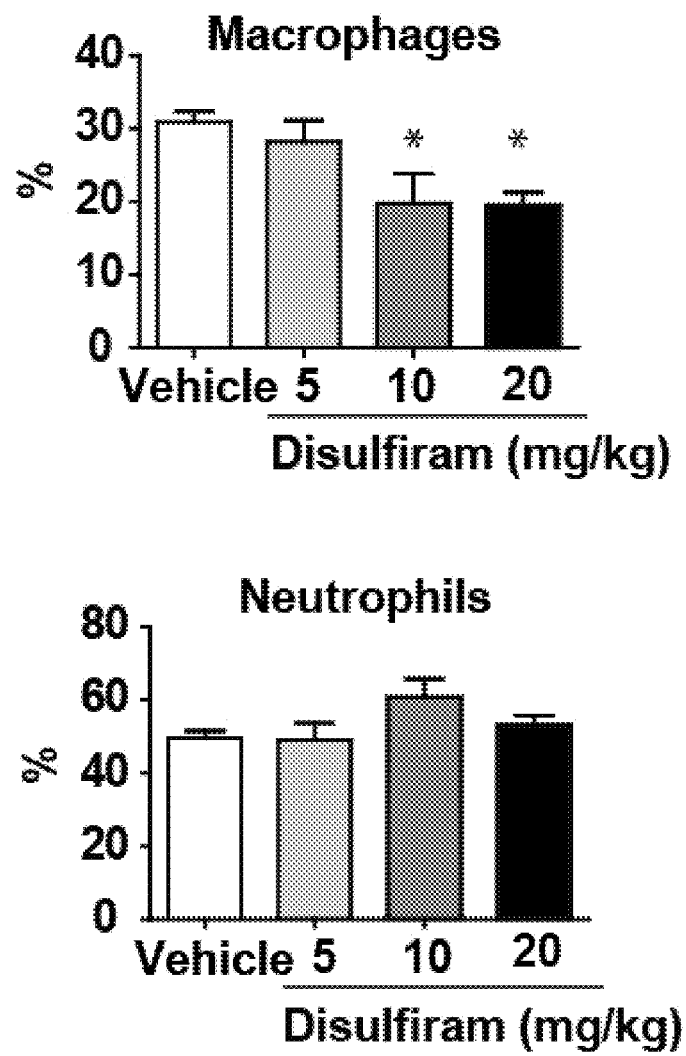
FIG. 10 shows the ratios of macrophages (left) and neutrophils (right) in cell populations collected from peritoneal inflammatory sites in wild-type mice to which disulfiram was administered. Disulfiram was administered to the mice at the doses shown in the figure.

Similarly as in the case of FROUNT-deficient mice, infiltration of macrophages into peritoneal inflammatory sites was reduced while infiltration of neutrophils was not influenced in the wild-type mice which received the FROUNT inhibitor disulfiram (FIG. 10).

10. Disulfiram Inhibits Cell Migration

[Methods]

In Vitro Chemotaxis Assay

A human leukocyte cell line THP-1 was counted and resuspended in Boyden buffer (RPMI medium supplemented with 0.1% BSA), and the cells were preincubated with disulfiram before the chemotaxis assay. The cell migration activity was measured using a 96-well ChemoTX Chemotaxis Chamber (Neuro probe) with a polycarbonate filter with a pore size of 5 Chemokine was applied to the lower chamber of the plate, and the cells were applied to the upper chamber. After incubation at 37° C. in 5% $CO_2$ for 90 minutes, the filter was removed, and the number of migrated cells in the lower chamber was counted using Cell Counting Kit F (Dojindo Laboratories).

[Results]

Figure 11:
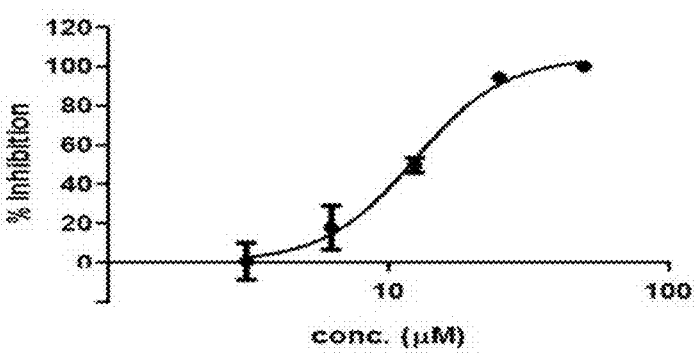
FIG. 11 shows the result of in vitro investigation of the cell migration-inhibiting activity of disulfiram using a human leukocyte cell line THP-1.

By treatment with disulfiram at a concentration at which it does not exhibit cytotoxicity (data not shown), cell migration mediated by CCL2 was inhibited (FIG. 11).

11. Disulfiram Inhibits Accumulation of Macrophages in Tumor Sites

[Methods]

Flow Cytometry

Lung cells of the lung metastasis model of wild-type mice described in the section 4 above or lung cells of the lung metastasis model of FNT-cKO mice and $FNT^{flox/flox}$ mice described in the section 7(2) above were obtained from the right lower lobe by digestion with collagenase and DNase. The cells were washed with PBS supplemented with 2% fetal bovine serum, resuspended, and filtered through a 70-µm strainer. The Fc receptor was blocked by incubation with an anti-mouse CD16/32 antibody (BD biosciences), and thereafter the cells were stained with a fluorescently labeled antibody. Anti-mouse CD11b-Brilliant Violet 510, anti-mouse Ly6C-APC-Cy7, and anti-mouse Ly6G-Alexa Fluor 700 were purchased from Biolegend. The stained cells were analyzed using the Gallios flow cytometer (Beckman coulter).

Immunohistochemical Staining

Each mouse was perfused with PBS, and the left lung was isolated. Optimal Cutting Temperature Compound (OCT) (Sakura Finetek) was injected from the trachea to embed the lung in OCT, and the lung was then frozen in liquid nitrogen. Fresh frozen sections with a thickness of 8 μm were prepared, and fixed with 4% paraformaldehyde-PBS. After washing with 0.05% Tween 20-PBS, the sections were blocked with Blocking One reagent (Nacalai Tesque), and sequentially stained with an anti-mouse F4/80 antibody (BioLegend) and Alexa Fluor 594 anti-rat IgG (Life technologies). Fluorescence Images were obtained with an SP5 confocal microscope (Leica Microsystems).

[Results]

Figure 12:
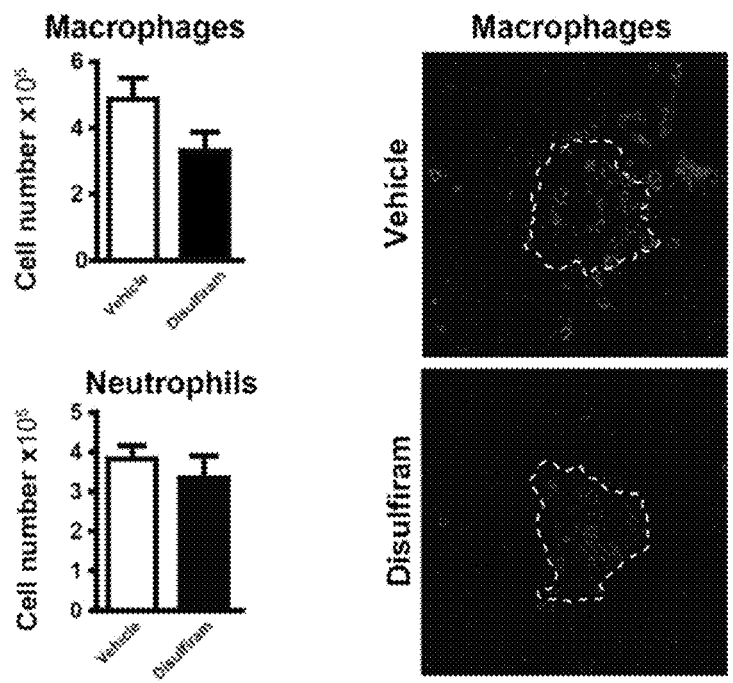
FIG. 12 shows the numbers of macrophages and neutrophils in lung metastasis in each group of mice receiving solvent treatment or disulfiram treatment investigated by flow cytometry (left), and accumulation of macrophages in the vicinity of metastatic nodules investigated by immunohistochemical staining (right). The broken lines in the immunostaining images indicate the positions of tumor metastatic lesions.

In the wild-type mice which received the FROUNT inhibitor disulfiram, accumulation of macrophages in tumor sites was reduced, compared to mice which received a solvent (FIG. 12). Also in the FROUNT-deficient mice, accumulation of macrophages in cancer metastatic nodules was significantly reduced compared to the non-deficient mice (data not shown).

The above-described results confirmed that mice to which the FROUNT inhibitor disulfiram was administered showed the same phenotypes as FROUNT-deficient mice, that is, inhibition of cancer hyperplasia, inhibition of cancer metastasis, and inhibition of macrophage infiltration into inflammatory sites.

12. Effect of Combined Use of Disulfiram and Anti-PD-1 Antibody

[Methods]

To provide an example of combined use of an anticancer drug and disulfiram (DSF), the effect of combined use of an anti-PD-1 antibody, which is an anticancer drug targeting an immune checkpoint molecule, and DSF was studied using an LLC tumor-bearing model and a B16 tumor-bearing model. The B16 tumor-bearing model was prepared by transplanting $5 \times 10^5$ B16 melanoma cells to the right abdomen of each of wild-type C57BL/6 mice. Preparation of the LLC tumor-bearing model was carried out in the same manner as in the above-described section 3. A feed supplemented with DSF was provided in the same manner as in the above-described section 3.

The day of the transplantation of the tumor cells to the mice was defined as Day 0. From Day 4, the mice were fed with the feed supplemented with DSF or a control feed every day during the experimental period. An anti-PD-1 antibody (J43, manufactured by BioXcell) was intraperitoneally administered once at a dose of 0.2 mg on each of Day 5, Day 8, Day 14, and Day 18 (four times in total). To provide a control for the antibody administration, PBS was intraperitoneally administered. The tumor size was measured using a caliper twice a week, and the tumor volume was calculated.

[Results]

Figure 13:
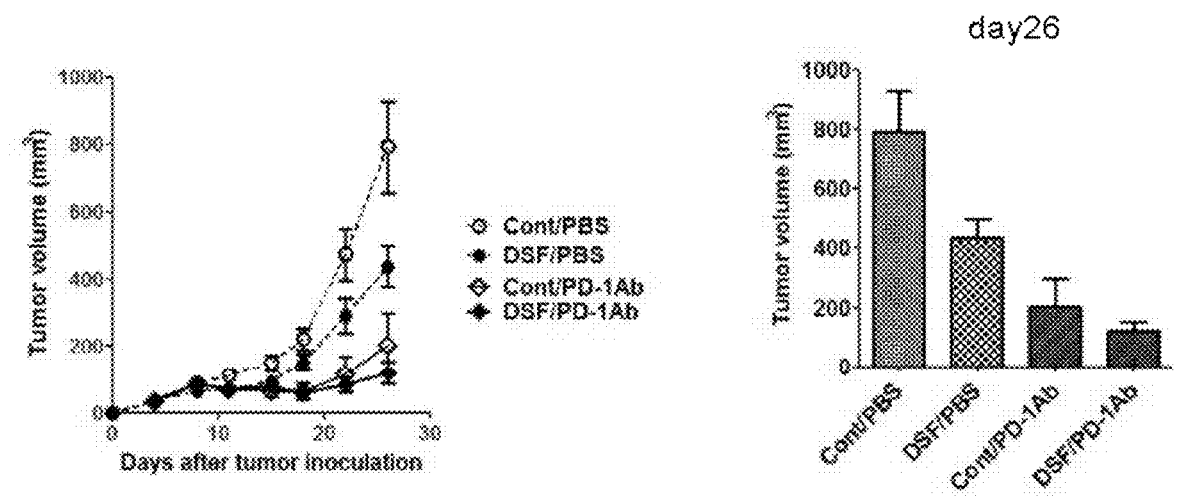
FIG. 13 shows the effect of combined use of disulfiram (DSF) and an anti-PD-1 antibody investigated in an LLC tumor-bearing model. The left panel shows changes in the tumor volume with time, and the right panel shows the tumor volume on Day 26 post tumor cell transplantation. Cont/PBS indicates a non-administration group; DSF/PBS indicates a DSF administration group; Cont/PD-1Ab indicates an anti-PD-1 antibody administration group; and DSF/PD-1Ab indicates a DSF+anti-PD-1 antibody combination group.

The result obtained from the LLC tumor-bearing model is shown in FIG. 13. In the LLC tumor-bearing model, administration of either one of an anti-PD-1 antibody and DSF inhibited hyperplasia of cancer cells, and combined administration of them showed an additive effect, confirming that the effect of an anti-PD-1 antibody to inhibit cancer hyperplasia was additively enhanced by the combined use with DSF.

Figure 14:
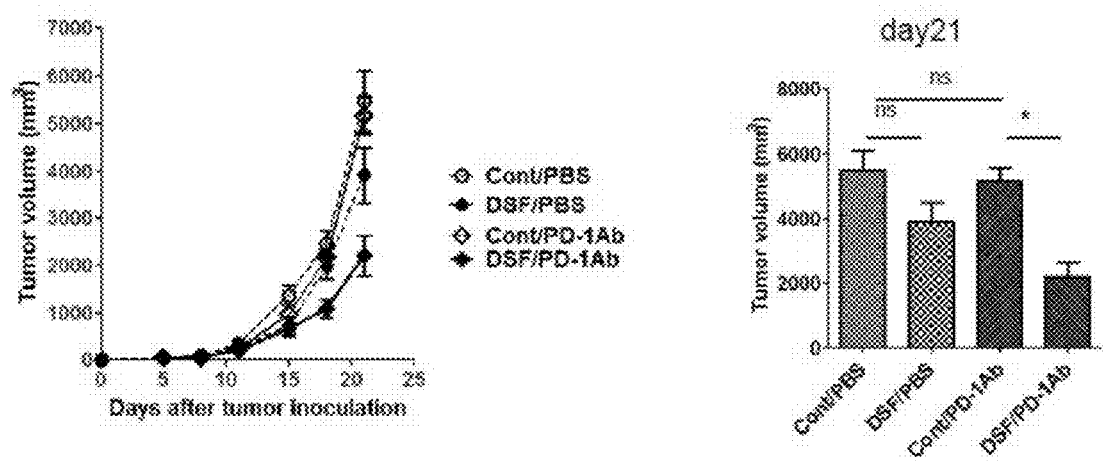
FIG. 14 shows the effect of combined use of disulfiram (DSF) and an anti-PD-1 antibody investigated in a B16 tumor-bearing model. The left panel shows changes in the tumor volume with time, and the right panel shows the tumor volume on Day 21 post tumor cell transplantation. Cont/PBS indicates a non-administration group; DSF/PBS indicates a DSF administration group; Cont/PD-1Ab indicates an anti-PD-1 antibody administration group; and DSF/PD-1Ab indicates a DSF+anti-PD-1 antibody combination group. ns, no significant difference; *, significant difference at $p<0.05$.

The result obtained from the B16 tumor-bearing model is shown in FIG. 14. In the B16 tumor-bearing model, an inhibitory effect on cancer hyperplasia was not observed at a significant level when an anti-PD-1 antibody or DSF was administered alone, but combined use of them evidently inhibited hyperplasia of cancer cells, confirming that a synergistic effect was obtained.

13. Effect of Combined Use of Disulfiram and Anti-CD4 Antibody

[Methods]

To provide another example of combined use of an anticancer drug and DSF, the effect of combined use of an anti-CD4 antibody having high cytotoxic activity and DSF was studied using an LLC tumor-bearing model and a B16 tumor-bearing model. The LLC tumor-bearing model and the B16 tumor-bearing model were prepared in the same manner as in the above-described section 12. A feed supplemented with DSF was provided in the same manner as in the above-described section 12. After the transplantation of the tumor cells, the tumor size was measured using a caliper twice a week, and the tumor volume was calculated.

The day of the transplantation of the tumor cells to the mice was defined as Day 0. From Day 4, the mice were fed with the feed supplemented with DSF or a control feed every day during the experimental period. An anti-CD4 antibody (GK1.5, an antibody known to be capable of depletion of CD4+ cells in the mouse body by the CDC activity; manufactured by BioXcell) was intraperitoneally administered once at a dose of 0.2 mg on each of Day 5 and Day 8 (two times in total). To provide a control for the antibody administration, PBS was intraperitoneally administered.

[Results]

Figure 15:
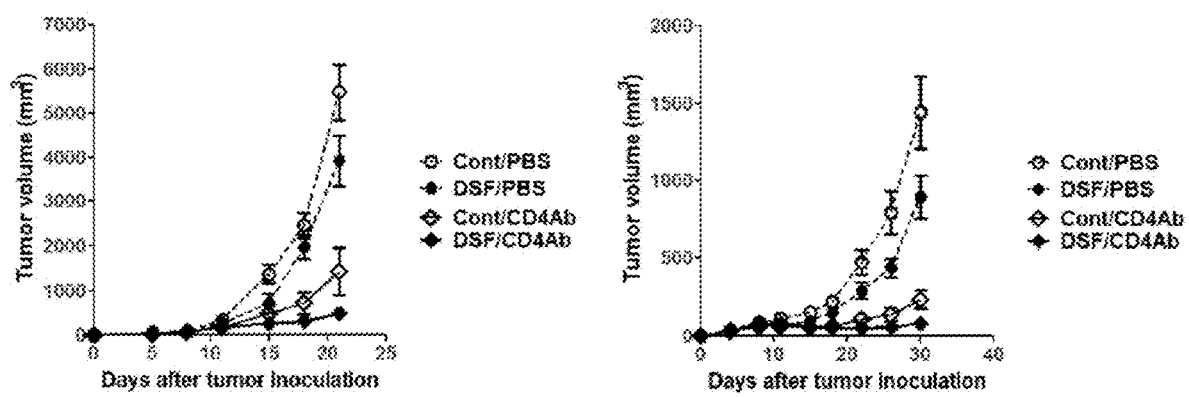
FIG. 15 shows the effects of combined use of disulfiram (DSF) and an anti-CD4 antibody investigated in an LLC tumor-bearing model (left) and in a B16 tumor-bearing model (right). Cont/PBS indicates a non-administration group; DSF/PBS indicates a DSF administration group; Cont/CD4Ab indicates an anti-CD4 antibody administration group; and DSF/CD4Ab indicates a DSF+anti-CD4 antibody combination group.

The result of measurement of the tumor volume with time is shown in FIG. 15. In both the LLC tumor-bearing model (left) and the B16 tumor-bearing model (right), the effect of the anti-CD4 antibody to inhibit cancer hyperplasia was confirmed to be significantly enhanced by the combined use with DSF.

The invention claimed is:

1. A method of treating melanoma, comprising administering an effective amount of disulfiram in combination with an antagonistic anti-PD-1 antibody to a subject in need thereof.

* * * * *